US009772227B2

(12) United States Patent
Scott et al.

(10) Patent No.: US 9,772,227 B2
(45) Date of Patent: Sep. 26, 2017

(54) LASER SPIDERWEB SENSOR USED WITH PORTABLE HANDHELD DEVICES

(71) Applicant: California Institute of Technology, Pasadena, CA (US)

(72) Inventors: David C. Scott, Pasadena, CA (US); Alexander Ksendzov, La Crescenta, CA (US); Warren P. George, Valencia, CA (US); James A. Smith, Granada Hills, CA (US); Abdullah S. Aljabri, Pasadena, CA (US); Joel M. Steinkraus, Azusa, CA (US); Rudi M. Bendig, Simi Valley, CA (US); Douglas C. Hofmann, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/864,613

(22) Filed: Sep. 24, 2015

(65) Prior Publication Data
US 2016/0084707 A1    Mar. 24, 2016

Related U.S. Application Data

(60) Provisional application No. 62/054,800, filed on Sep. 24, 2014.

(51) Int. Cl.
  *G01N 21/00* (2006.01)
  *G01J 3/02* (2006.01)
  *G01J 3/42* (2006.01)

(52) U.S. Cl.
  CPC ............. *G01J 3/0291* (2013.01); *G01J 3/021* (2013.01); *G01J 3/42* (2013.01); *G01J 3/0256* (2013.01);
  (Continued)

(58) Field of Classification Search
  CPC ............. G01N 2333/59; G01N 33/558; G02B 17/023; G02B 2027/0154; G02B 25/002;
  (Continued)

(56) References Cited

U.S. PATENT DOCUMENTS

| 5,412,474 A * | 5/1995 | Reasenberg ....... G01B 9/02002 356/4.09 |
| 2008/0111993 A1 * | 5/2008 | Miller .................... G01N 21/39 356/437 |

(Continued)

OTHER PUBLICATIONS

"Handheld Volatile Organic Compound (VOC) Meter", http://www.omega.com/pptst/HHAQ-107.html, downloaded May 23, 2016.

(Continued)

*Primary Examiner* — Michael P Stafira
(74) *Attorney, Agent, or Firm* — Gates & Cooper LLP

(57) ABSTRACT

A portable spectrometer, including a smart phone case storing a portable spectrometer, wherein the portable spectrometer includes a cavity; a source for emitting electromagnetic radiation that is directed on a sample in the cavity, wherein the electromagnetic radiation is reflected within the cavity to form multiple passes of the electromagnetic radiation through the sample; a detector for detecting the electromagnetic radiation after the electromagnetic radiation has made the multiple passes through the sample in the cavity, the detector outputting a signal in response to the detecting; and a device for communicating the signal to a smart phone, wherein the smart phone executes an application that performs a spectral analysis of the signal.

21 Claims, 20 Drawing Sheets

(52) U.S. Cl.
CPC ........ *G01J 2003/423* (2013.01); *G01N 21/00* (2013.01)

(58) Field of Classification Search
CPC .. G02B 25/005; G02B 25/02; G02B 27/0101; G02B 27/0149; G02B 27/027; G02B 27/028; G02B 27/04; G02B 27/2292; G02B 5/09
See application file for complete search history.

(56) References Cited

U.S. PATENT DOCUMENTS

| | | | |
|---|---|---|---|
| 2012/0225475 A1* | 9/2012 | Wagner | G01N 15/14 435/288.7 |
| 2013/0139964 A1 | 6/2013 | Hofmann et al. | |
| 2014/0168649 A1* | 6/2014 | Smith | G01J 3/0291 356/409 |
| 2015/0015780 A1* | 1/2015 | Graham | H04N 5/2252 348/376 |

OTHER PUBLICATIONS

Hofmann, D.C., et al., "Designing metallic glass matrix composites with high toughness and tensile ductility", vol. 451, Feb. 28, 2008, nature, doi:10.1038/nature 6598.

Phillips, M.C., et al., "Measurement of Broad Absorption Features Using a Tunable External Cavity Quantum Cascade Laser", Proc. SPIE Int. Soc. Opt. Eng. 6760, 676003 (2007).

Scott, D.C., et al., "Airborne Laser Infrared Absorption Spectrometer (ALIAS-II) for in situ atmospheric measurements of N2O, CH4, CO, HCl, and NO2 from balloon or remotely piloted aircraft platforms," Applied Optics, 38, 4609-4622 (1999).

Tarsitano, C.G., et al., "Multilaser Herriott cell for planetary tunable laser spectrometers", Applied Optics, 46, 6923-6935 (2007).

Webster, C.R., et al., "Aircraft (ER-2) Laser Infrared Absorption Spectrometer (ALIAS) for In-situ Stratospheric Measurements of HCl, N2O, CH4, NO2, and HNO3", Applied Optics 33, 454-472 (1994).

"Disease Markers in Exhaled-Breath", edited by Nandor Marczin, et al., CRC Press (2002), ISBN 9780203909195-CAT# HE00047.

http://oco.jpl.nasa.gov/ downloaded on Sep. 23, 2015.

http://pinestreetfoundation.org/research/canine/ downloaded on Sep. 23, 2015.

Chernin, S., "New generation of multipass systems in high resolution spectroscopy", Spectrochimica Acta Part A, 1996, pp. 1009-1022, vol. 52.

Chernin, S., "Multipass annular mirror system for spectroscopic studies in shock tubes", Journal of Modern Optics, Jan. 20, 2004, pp. 223-231, vol. 51, No. 2.

* cited by examiner

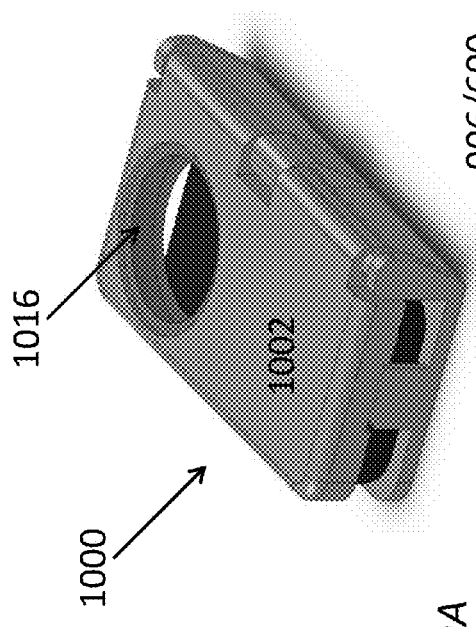
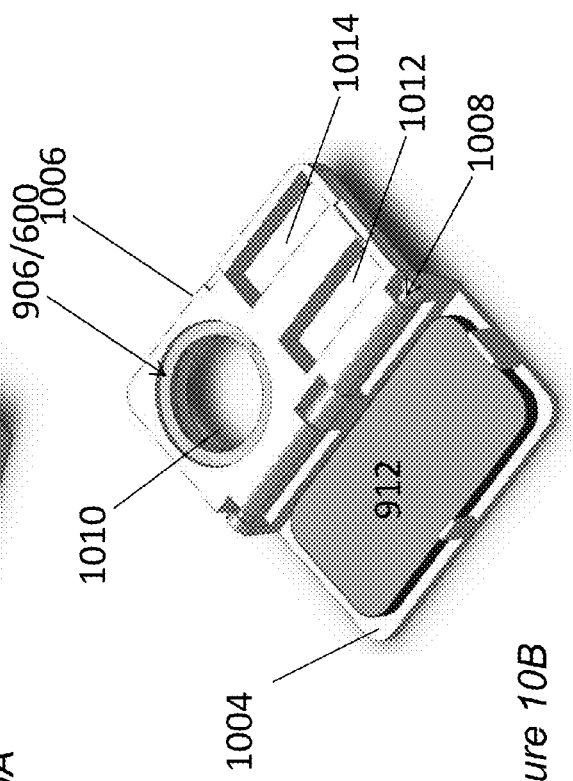
Figure 10A
Figure 10B

LASER SPIDERWEB SENSOR USED WITH PORTABLE HANDHELD DEVICES

CROSS REFERENCE TO RELATED APPLICATIONS

This application claims the benefit under 35 U.S.C. Section 119(e) of co-pending and commonly-assigned U.S. Provisional Patent Application Ser. No. 62/054,800, filed on Sep. 24, 2014, by David C. Scott, Alexander Ksendzov, Warren P George, Richard L. Baron, James A. Smith, Abdullah S. Aljabri, Joel M. Steinkraus, and Rudi M Bendig, entitled "LASER SPIDERWEB SENSOR USED WITH PORTABLE HANDHELD DEVICES," which application is incorporated by reference herein.

STATEMENT REGARDING FEDERALLY SPONSORED RESEARCH AND DEVELOPMENT

The invention described herein was made in the performance of work under a NASA contract, and is subject to the provisions of Public Law 96-517 (35 USC 202) in which the Contractor has elected to retain title.

BACKGROUND OF THE INVENTION

1. Field of the Invention

This invention relates to a spectrometer and method of fabricating a spectrometer.

2. Description of the Related Art (Note: This application references a number of different publications as indicated throughout the specification by one or more reference numbers within brackets, e.g., [x]. A list of these different publications ordered according to these reference numbers can be found below in the section entitled "References." Each of these publications is incorporated by reference herein.)

Detection of chemicals important in the global carbon cycle and climate monitoring are of paramount importance to the Department of Energy (DOE), the Environmental Protection Agency (EPA), the Department of Transportation (DOT) and NASA. The mission of the Biological and Environmental Research (BER) program at the DOE is to understand complex biological, climatic, and environmental systems across spatial and temporal scales ranging from sub-micron to the global, from individual molecules to ecosystems, and from nanoseconds to millennia. This is accomplished by discovering the physical, chemical, and biological drivers of climate change; and seeking the molecular determinants of environmental sustainability and stewardship.

Chemical detection also has application in medicine, for example, in identification of disease markers.

SUMMARY OF THE INVENTION

One or more embodiments of the invention disclose a portable spectrometer, comprising a smart phone case or portable computer case storing a portable spectrometer, wherein the portable spectrometer includes a cavity; a source for emitting electromagnetic radiation that is directed on the sample in the cavity, wherein the electromagnetic radiation is reflected within the cavity to form multiple passes of the electromagnetic radiation through the sample; and a detector for detecting the electromagnetic radiation after the electromagnetic radiation has made the multiple passes through the sample in the cavity, the detector outputting a signal in response to the detecting and communicating the signal to a smart phone or portable computer, and the smart phone or portable computer executing an application that performs a spectral analysis of the signal. Thus, one or more processors in the smart phone can form an output identifying a composition of the sample (e.g., the sample that enters, is contained in, is enclosed by, or is defined by, the cavity).

The cavity can include a ring having an elliptical inner surface. The cavity can include an inner surface substantially described by the equation:

$$\frac{x^2 + y^2}{a^2} + \frac{z^2}{c^2} = 1,$$

wherein x, y, and z are Cartesian coordinates, a is an equatorial radius comprising a maximum value of x and y, c is a distance along the z- axis from coordinate (x=0, y=0, z=0) to a pole of the spheroid described by the equation, and a≠c.

The electromagnetic radiation incident on the inner surface can be reflected from multiple regions of the inner surface such that the multiple passes of the electromagnetic radiation through the sample in the cavity are formed.

The cavity can be dimensioned such that a volume of the cavity comprising the sample is between 33 mm$^3$ and 905000 mm$^3$. The cavity can have a height in a range of 2 millimeters (mm)-20 mm, a width of 2 mm-60 mm, and a length of 2 mm-60 mm, for example. In one or more embodiments (referring to the equation as a function of x, y, and z above), z<c, z is in a range of 2 mm-20 mm, and a is in a range of 2 mm-60 mm. In one or more embodiments, an angle of incidence of the electromagnetic radiation, at a first reflection within the cavity, is between more than 0 degrees and 45 degrees, a is less than 60 mm, z is less than 20 mm, and the angle of incidence, a, and z are such that a total path length of the electromagnetic radiation transmitted through the sample includes a distance of 30 meters. An angle of incidence of the electromagnetic radiation at a first reflection within the cavity, a, and z can be selected such that the spectrometer can identify the sample having a relative concentration in the cavity of 50 parts-per-billion by volume (ppbv).

The cavity can further comprise one or more windows through which the electromagnetic radiation is inputted into the cavity and through which the electromagnetic radiation exits the cavity after a last pass of the electromagnetic radiation through the sample, the detector positioned to receive the electromagnetic radiation after the last pass.

The smart phone case further comprise a first wing storing the smart phone; a second wing storing the portable spectrometer; and a hinge connecting the first wing to the second wing, wherein the hinge folds the smart phone case so that the second wing is superposed on the first wing when the smart phone case is closed. The first wing can have substantially a same surface area as the smart phone and the second wing has substantially a same size as the portable spectrometer. When the smart phone case is closed, the smart phone case can have a length of 30 centimeters (cm) or 15 cm or less, a width of 30 cm or 15 cm or less, and a thickness of 4 cm or less.

The second wing can comprise a first opening or attachment for holding the cavity, a second opening or attachment for holding the source, a third opening or attachment for holding the detector, and one or more additional openings through which the laser beam is transmitted to the cavity from the source and from the cavity to the detector.

The portable spectrometer can further comprise an optical interfacing system, wherein the optical interfacing system guides the electromagnetic radiation into the cavity at an appropriate angle to achieve a desired number of the multiple passes, guides the electromagnetic radiation after the number of passes onto the detector, and is stored in the smart phone case.

The spectrometer can further comprise support electronics for the detector and support electronics for the laser.

The cavity and/or case assemblies can comprise or consist essentially of bulk metallic glass or bulk metallic glass matrix composite.

One or more embodiments of the invention further disclose a method of fabricating a smart phone case, comprising molding a material (e.g., bulk metallic glass or bulk metallic glass composite) into a smart phone case wherein the smart phone case is capable of holding the smart phone and the portable spectrometer such that the portable spectrometer can operate and perform a spectral analysis of the sample. For example, the molding can comprise molding the smart phone case wherein the cavity comprises a molded surface of the smart phone case and the electromagnetic radiation is reflected from the molded surface to form the multiple passes of the electromagnetic radiation through the sample during operation of the spectrometer.

One or more embodiments of the invention further disclose an article of manufacture or spectrometer comprising a ring cavity, the ring/ring cavity comprising a reflective inner surface described by the equation:

$$\frac{x^2 + y^2}{a^2} + \frac{z^2}{c^2} = 1,$$

wherein x, y, and z are Cartesian coordinates, a is an equatorial radius comprising a maximum value of x and y, c is a distance along the z- axis from coordinate (x=0, y=0, z=0) to a pole of the spheroid described by the equation, and a≠c. One or more openings are cut in the inner surface for one or more windows. A laser beam incident on the elliptical inner surface through the one or more windows is reflected from multiple regions of the reflective inner surface such that multiple passes of the laser beam through a sample surrounded by the elliptical inner surface are formed, and detection of the laser beam reflected from the multiple regions and received on a detector through the one or more windows can be used to identify the sample.

BRIEF DESCRIPTION OF THE DRAWINGS

Referring now to the drawings in which like reference numbers represent corresponding parts throughout:

FIGS. 6A-6F illustrate a laser ring spectrometer geometry, according to one or more embodiments of the invention, wherein FIG. 6A illustrates a first side view, FIG. 6B illustrates a second side view, FIG. 6C illustrates a top view, FIG. 6D and FIG. 6E illustrate perspective views, FIG. 6F shows a magnified view of a section of the ring;

FIGS. 6I-6M illustrate a laser ring spectrometer geometry designed for spaceflight, according to one or more embodiments of the invention, wherein FIG. 6I illustrates a first side view, FIG. 6J illustrates a second side view, FIG. 6K illustrates a top view, FIG. 6L illustrates a perspective view, and FIG. 6M shows a magnified view of a section of the ring;

FIGS. 10A and 10B illustrate a smart phone architecture for the LSS including a case for housing the smart phone and the LSS, according to one or more embodiments of the invention;

DETAILED DESCRIPTION OF THE INVENTION

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Technical Description

Introduction Current state of the art systems using Gas Chromatography—Mass Spectrometry (GC/MS), Surface Acoustic Wave (SAW) sensors, Ion Mobility Spectrometers (IMS), Laser Induced Fluorescence (LIF), and other systems, are large, use consumables, and require large quantities of power. Laser spectrometers offer a tremendous improvement over the current state of the art chemical detection systems in that they can be configured in an open path system that does not require inlet systems and pumps to introduce the sample to be analyzed into the spectrometer. Extensive work with the infrared spectral libraries funded by the National Nuclear Security Administration (NNSA), Defense Advanced Research Projects Agency (DARPA), and other government agencies enables direct comparison with the library data in real time to enable extremely high confidence detection of analytes.

In one or more embodiments, a laser spectrometer comprises a laser electromagnetically coupled to a cavity comprising a gaseous chemical sample or analyte, wherein the laser beam emitted from the laser has a frequency resonant with one or more known vibrational modes or one or more known absorption frequencies of one or more known chemical elements or compounds. A detector is electromagnetically coupled to the cavity to measure the laser beam after the laser beam has interacted with the sample. If the detector measures absorption corresponding to the known absorption frequency of the known compound, then the sample can be identified.

Recent advancements in laser spectrometers enable these systems to be implemented for facile detection of chemicals. Specifically, research for the NNSA has demonstrated the feasibility of detection of chemical weapons agents via that of simulants (Freons) with similar spectroscopic features [2]. This has been achieved using Freon-125 as a simulant, a tunable laser, and a Herriott cell-based sensor based on flight proven designs developed at the Jet Propulsion Laboratory (JPL) for use in earth and planetary exploration.

Figure 1:
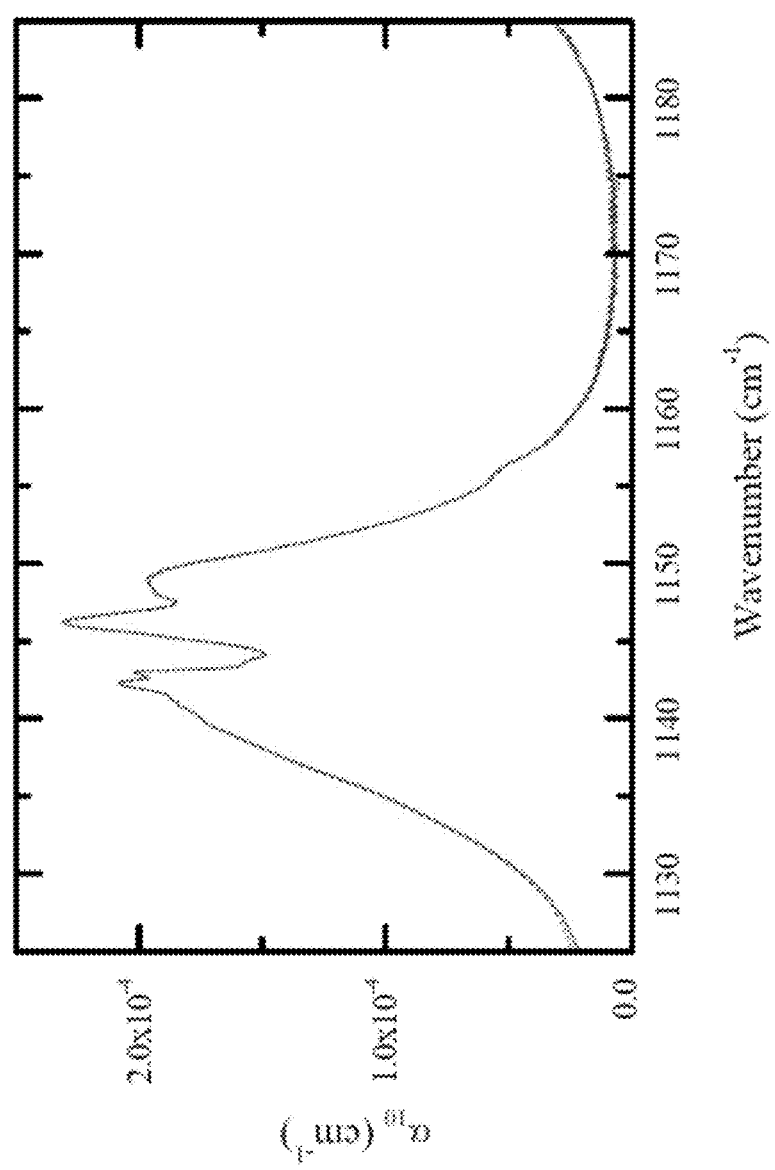
FIG. 1 shows a high resolution absorption spectrum of 10 parts per million (ppm) Freon-125, wherein the solid red line is the absorption spectrum measured using the External Cavity Quantum Cascade Laser (EC-QCL) and a Herriott cell configured for a path length of 47 m and the dashed blue line is a reference absorption spectrum obtained from the spectral library.

The experimentally obtained spectrum of this simulant shown in FIG. 1 matches that found in the spectral library extremely well, demonstrating the ability of this technique to detect the exact shape of the spectral feature, which in turn indicates the ability to recognize the simulant even in the presence of significant interference. It has also been demonstrated that the detected features of a typical interferent, namely water, are so different in shape and width as compared to the simulant, that they are easily recognized and separated from such a measurement.

Judging from the signal-to-noise ratio (SNR) of the experimental data obtained, the noise equivalent absorption sensitivity is estimated to be $0.5 \times 10^{-7}$ to $1 \times 10^{-6}$ cm$^{-1}$. For the particular feature of the simulant examined in this work, this corresponds to a relative concentration of 50 to 25 parts-per-billion by volume (ppbv). For applications requiring higher sensitivity, longer path lengths can be obtained using advanced spherical ring optical cavity designs. The corresponding relative concentrations of other chemical targets would differ depending on the particular transition strengths, and would thus have to be scaled accordingly. Targets of specific interest are $CO_2$, $CO$, $H_2O$, $CH_4$, $N_2O$ and $O_2$.

The first set is under observation for its role in global warming and its contribution to the greenhouse effect. Having a global network of portable detectors can yield invaluable information about the bulk movement and presence of greenhouse gases through observation of their localized behavior. Currently NASA's Orbiting Carbon Observatory (OCO-2) is taking similar measurements but from the vantage point of space. For this project, ground based data would be invaluable for validation.

In addition, detection of $O_2$ (and other other compounds and elements) is important when monitoring healthy working conditions. Low levels of $O_2$ in a room decrease productivity levels and create a health hazard. Having portable monitors that can take precision measurements of both fluctuations and relative amounts of $O_2$, $CO_2$, $CO$ and $H_2O$ levels in a building would allow for a safer and more comfortable work place.

Cavity Design

Figure 2:
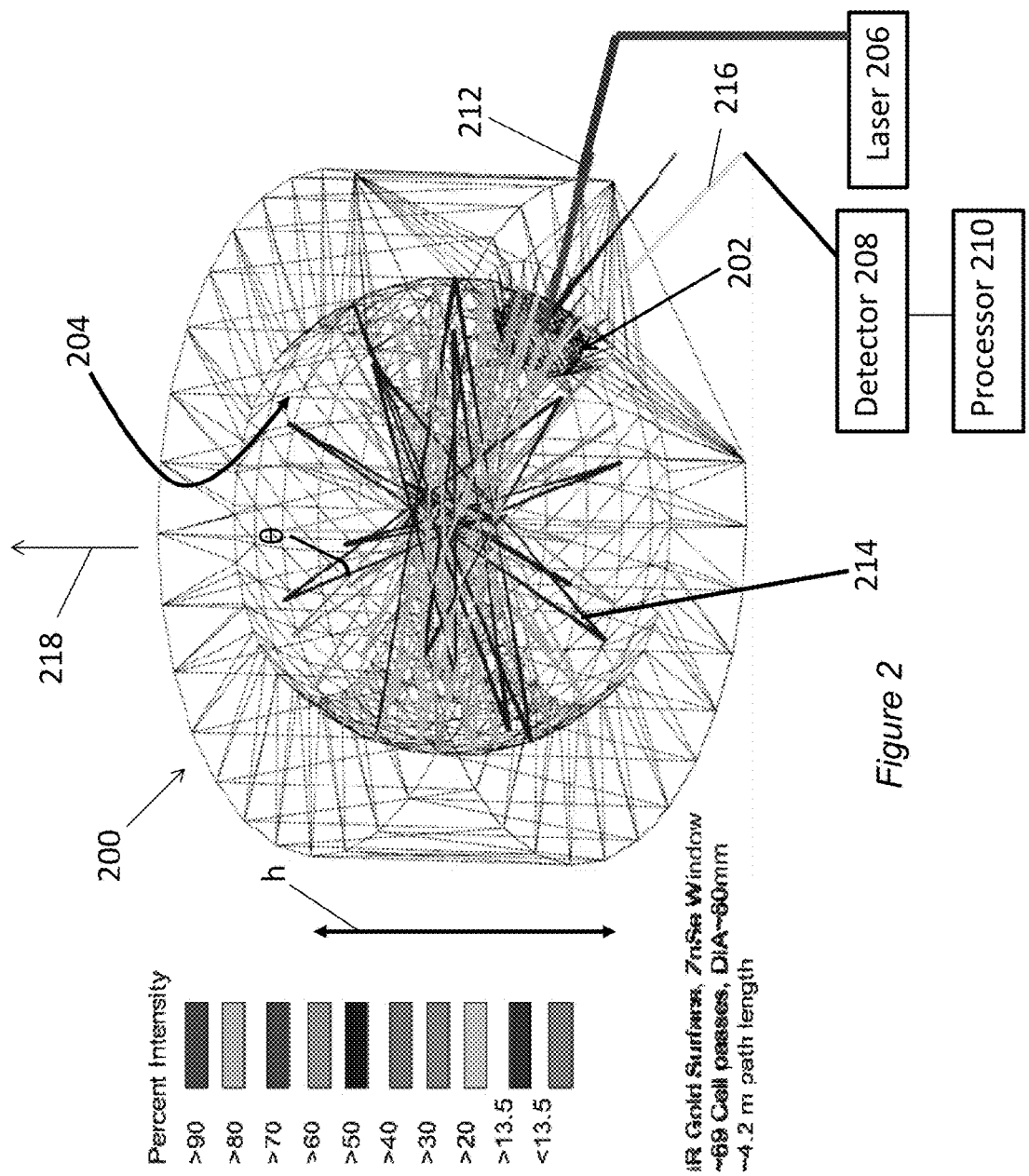
FIG. 2 illustrates a laser intensity model for three dimensional injection into a Laser Spider Web Sensor (LSS) according to one or more embodiments of the invention, wherein, for this configuration, the radius of curvature of the interior surface is greater than the internal diameter of the ring, generating an elliptical surface enabling a greater path length than a planar ring pattern (the intensity pattern is calculated using Tracepro™ optical ray trace software)

FIG. 2 illustrates a spectrometer according to one or more embodiments of the invention including a cavity 200 (e.g., into which a gaseous chemical sample or analyte is placed), one or more windows 202 in the cavity; a laser 206 electromagnetically coupled to the cavity 200; a detector 208 electromagnetically coupled to the cavity; and one or more processors 210 connected to the detector 210. A laser beam 212 (e.g., emitting infrared or terahertz electromagnetic radiation), outputted from the laser 206 and incident on the inner surface 204 through the one or more windows 202, is reflected from multiple regions of the inner surface 204 such that multiple passes of the laser beam 214 through a sample in the cavity are formed. The detector 208 (e.g., InGaAs detector) outputs a signal in response to detecting the laser beam 216 reflected from the multiple regions and received on the detector 208 through the one or more windows 202. The detector can be positioned to receive the electromagnetic radiation 216 after the last pass.

The laser beam 212 has a frequency resonant with one or more known vibrational modes or one or more known absorption frequencies of one or more known chemical elements or compounds. If the detector 208 measures absorption corresponding to the known absorption frequency of the known compound, then the sample can be identified. Thus, one or more processors connected to the detector can process the signal (by comparing the absorption of the sample to the absorption of a known compound) to form an output identifying the sample.

The laser can comprise a broadly tunable laser, e.g., quantum cascade laser, that can be tuned to emit electromagnetic radiation over a wavenumber range up to 65 cm$^{-1}$ or up to 100 cm$^{-1}$ from a center frequency corresponding to a wavelength in a range of 1 micrometer to 20 micrometers. The quantum cascade laser can use a grating to tune the frequency. The inner surface can comprise a mirror reflective surface (e.g., including a coating or optical coating, such as a gold coating) that can reflect over this frequency range.

In one or more embodiments of the invention, the resonate laser traces in the cavity form a web of coherent light ensuring complete sampling of the air in the target volume, and/or the multipass ring cell maps a linear cavity into a ring or circular cavity. As is the case with traditional Herriott cells, the inner surface comprising mirror surface in one or more examples can be entirely spherical or astigmatic, which produces dense Lissajous-type patterns that enable large path lengths. Like stable Herriott designs, the ring multipass cell according to one or more embodiments of the invention is self-imaging and constantly re-focuses the propagating beam as it reflects from surface to surface within the cavity.

FIG. 2 further illustrates an example of a ring cell with elliptical surfaces 204. For this configuration the radius of curvature of the interior surface 204 is greater than the internal diameter of the ring. This generates an elliptical surface 204 enabling a greater path length than a planar ring pattern (illustrated in FIG. 3) [13]. Specifically, FIG. 2 illustrates the inner/interior surface 204 of the cavity 200 comprising an elliptical surface of revolution about an axis 218 (e.g., wherein the generatrix is an ellipse or portion of an ellipse rotated 360 degrees about the central axis 218 passing through a center of the cavity). In this way, the surface of revolution can comprise a section of a spheroid/truncated spheroid/ellipsoid of revolution that can be bisected into two equal parts by a bisecting plane comprising one of the two semi-diameters of the spheroid.

In one or more embodiments of the invention, the inner/interior surface can be described by the equation:

$$\frac{x^2 + y^2}{a^2} + \frac{z^2}{c^2} = 1,$$

wherein x, y, and z are Cartesian coordinates in a Cartesian coordinate system having x, y, and z axes, a is a real number representing the equatorial radius (a maximum value of x and y), c is a real number representing a distance along the z-axis from coordinate (x=0, y=0, z=0) to a pole of the spheroid described by the equation, and a≠c. In one or more embodiments, z<c, z is in a range of 2 mm-20 mm, and/or a is in a range of 2 mm-60 mm.

The cavity height (h) can be made quite thin (<10 mm) to allow for modular units for different wavelengths of interest, and the shallow cell depth can avoid wall effects sometimes encountered with cells of the linear configuration.

The angle at which the laser beam 212 is inputted into the cavity (e.g., the angle with respect to the input surface of the window 202), the angle of incidence of the electromagnetic radiation on the inner surface 204 (at first and/or subsequent reflections within the cavity), and the angle θ between an incident beam and the subsequently reflected beam, can be selected to obtain a desired number of passes through the cavity. Together with the angle of incidence, a, and z can also be selected such that the spectrometer can identify the sample having a relative concentration in the cavity of 50 parts-per-billion by volume (ppbv) and/or such that a total path length of the electromagnetic radiation transmitted through the sample includes a specified minimum distance (e.g., 4 meters, 30 meters). For example, the angle of incidence of the electromagnetic radiation, at a first reflection within the cavity, can be between more than 0 degrees and 45 degrees, a can be less than 60 mm, and z can be less than 20 mm, such that a total path length of the electromagnetic radiation transmitted through the sample includes a distance of 4 meters or 30 meters.

Figure 3:
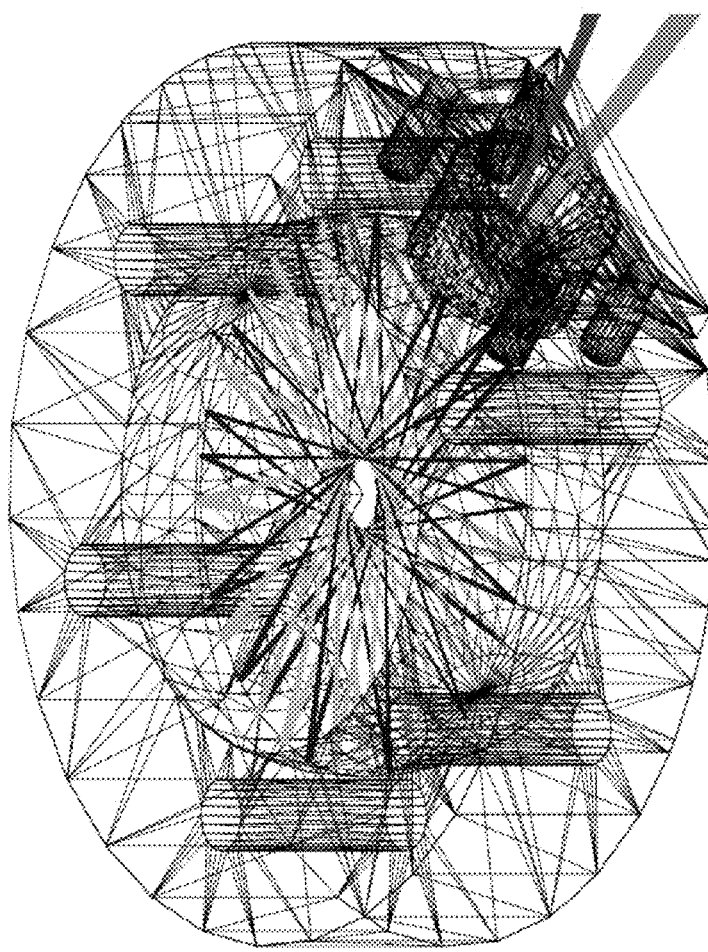
FIG. 3 illustrates a ray trace illustrating a specific condition for a 2 degree injection angle of a laser beam into a spherical ring according to one or more embodiments of the invention, wherein the number of round trips inside the spherical ring can be varied by changing the laser beam injection angle.
Figure 3:
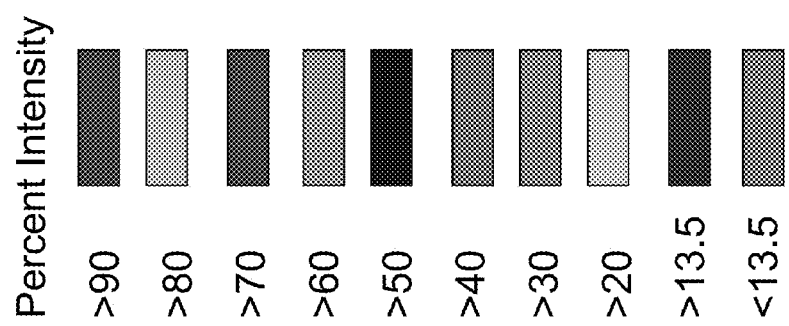

The colors or shading of the beams 214 in FIG. 2 (and FIG. 3) show how the intensity of the laser beam is attenuated as it is reflected by the inner surface 204 and as the number of passes/reflections 214 through the cavity is increased. At the input, the laser beam 212 has more than 90% of the initial intensity (at the laser output). At the output, the laser beam 216 has more than 20% of the initial intensity (calculated for an inner surface 204 comprising a gold surface coated for an infrared laser beam 206, a ZnSe window 202, a cavity 200 having an inner diameter of 2a=60 mm, and an angle θ wherein the laser makes ~69 passes through the cell before exiting the cell, corresponding to a ~4.2 meter (m) path length of the laser beam through the cavity 200). In FIG. 3, the ray trace analysis is for an inner surface comprising a gold surface coated for an infrared (IR) beam, a ZnSe window, and a cavity having an inner diameter of 50 mm, and the ray trace analysis shows the laser beam inputted into the cavity makes ~37 passes through the cell before exiting the cell (corresponding to a ~1.85 m path length of the laser beam through the cavity).

Figure 4:
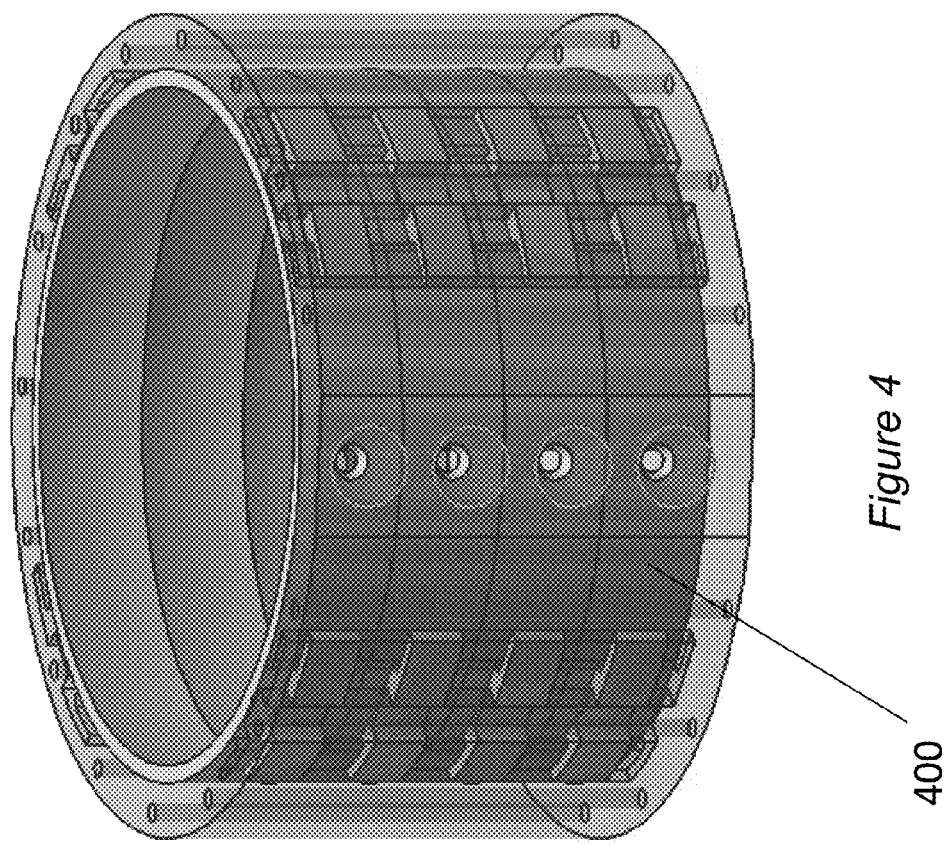
FIG. 4 illustrates an ultralight four channel system developed for chemical detection and according to one or more embodiments of the invention, comprising aluminum rings coated with gold on chrome and encased in a carbon fiber shell.

Stacking multiple rings allows tailoring the detection suite of chemicals to meet the given application. Using interchangeable modular designs it is possible to tailor the detection system to cover a broad range of chemicals important to global climate change or other applications. FIG. 4 is a modular multichannel system in which four rings 400 (theoretically operating four different wavelengths) are stacked together in order to detect multiple gas species as the airflow passes through.

Manufacturing and Assembly Procedure

Figure 5:
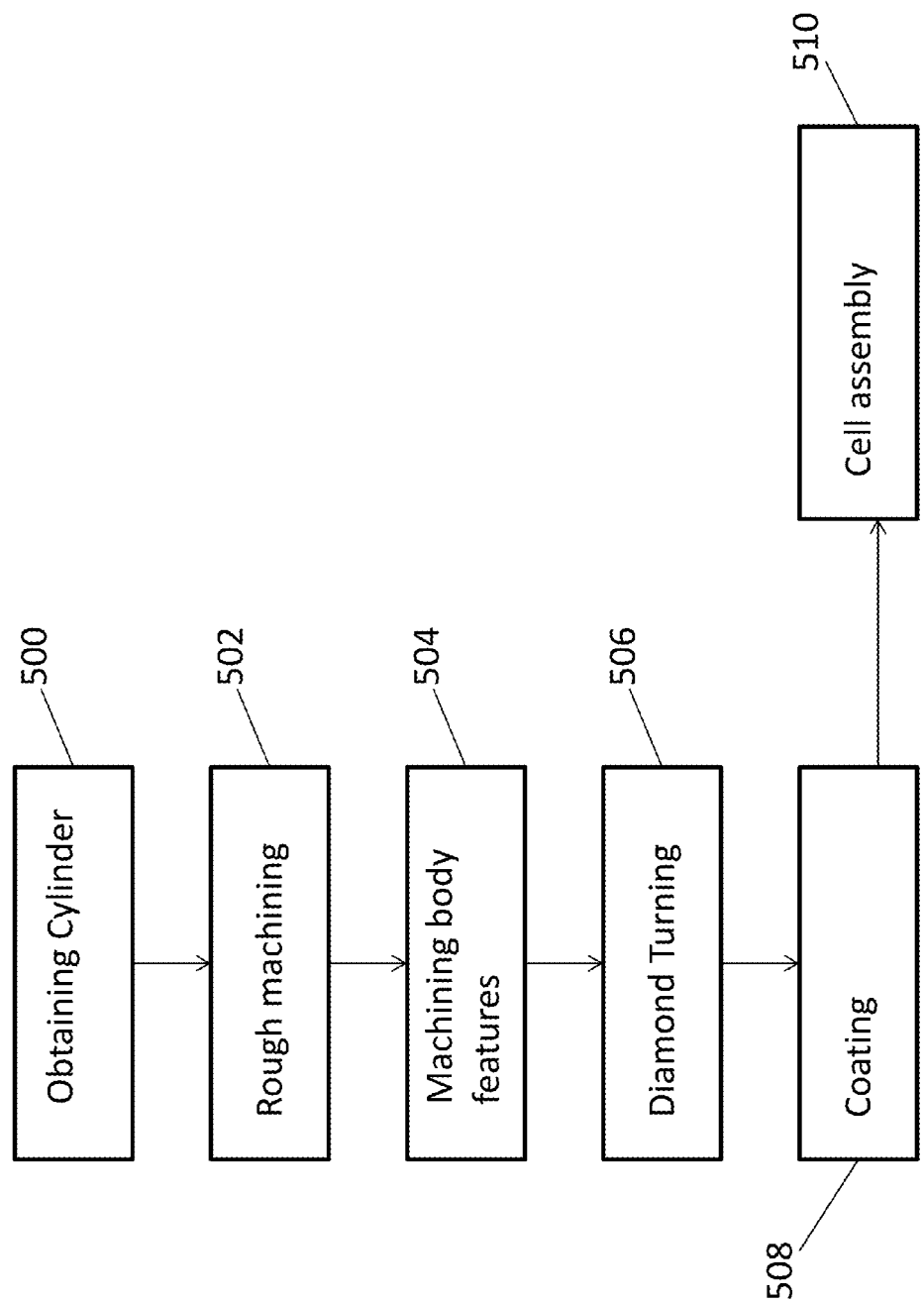
FIG. 5 is a flowchart illustrating a method of fabricating a ring cavity and absorption cell according to one or more embodiments of the invention.

FIG. 5 illustrates a method of fabricating the ring cavity 600 (illustrated in FIGS. 6A-6F) and calibration cell 700 (illustrated in FIGS. 7A-7B), according to one or more embodiments of the invention.

Block 500 represents obtaining a 6061 Aluminum metal cylinder. However other metal or materials could be used.

Block 502 represents rough machining the ring reflecting surface 602 with a 5 axis computer numerical control (CNC) mill, wherein the rough cut should leave a maximum of 0.005" of material in excess of the final dimensions. However, in one or more embodiments, a different maximum of material in excess of the final dimensions could be used.

Block 504 represents machining all additional body features including mounting holes 604, 606, and window hole 608, etc., with the exception of the final ring surface 602 and the knife edges 610.

Block 506 represents diamond turning the inner surface/final ring surface 602 and knife edges 610 (e.g., at NiProOptics™).

Block 508 represents applying (e.g., at NiProOptics) a gold surface coating across the inner face/final ring surface 602 of the ring 600. The surface can be shaped according to the elliptical surface 204 illustrated in FIG. 2 (or surface in FIG. 3), for example. The rings can be used as the rings 400 in FIG. 4.

Figure 6A:
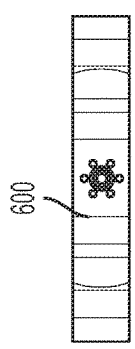
Figure 6B:
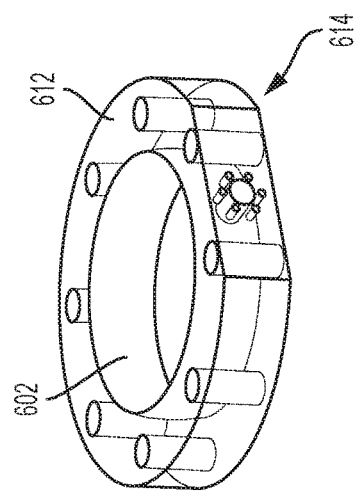
Figure 6C:
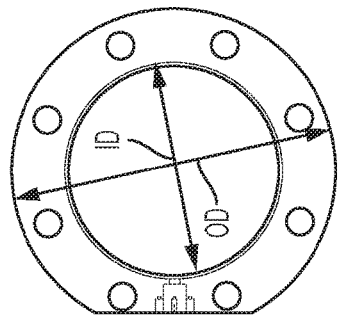
Figure 6D:
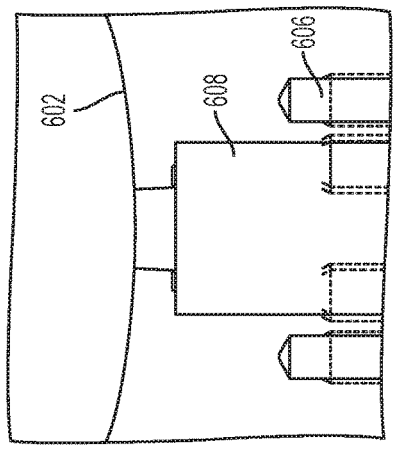
Figure 6E:
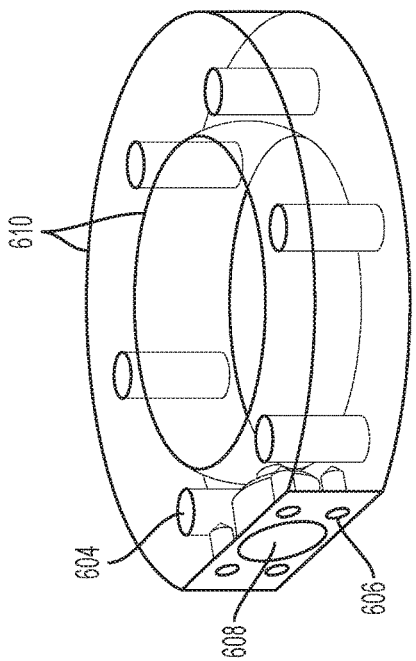
Figure 6F:
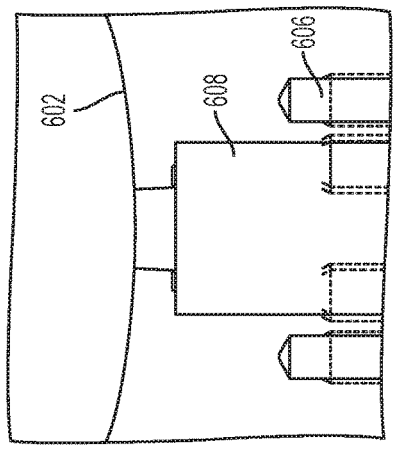
Figure 6G:
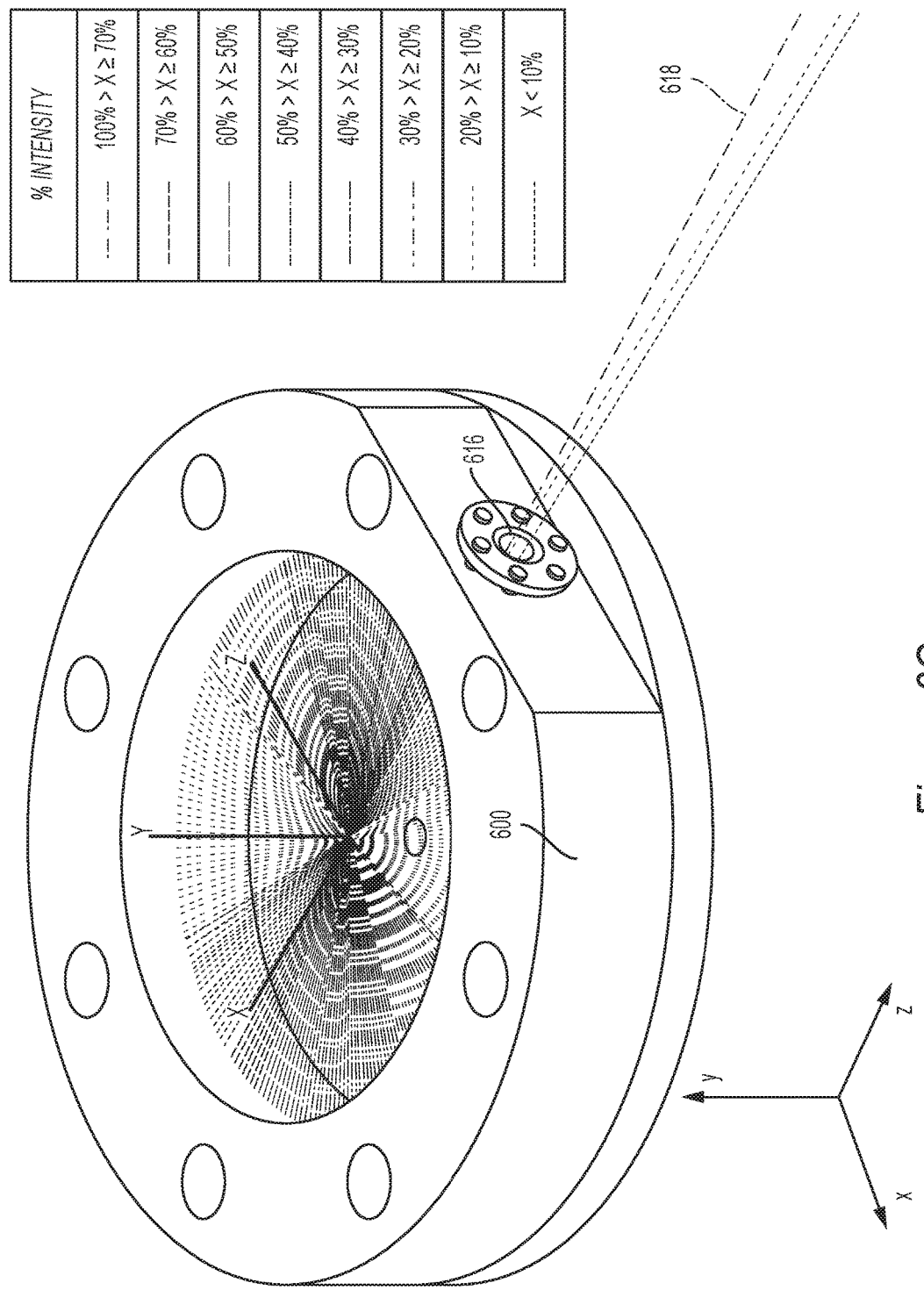
FIG. 6G shows a Tracepro™ optical analysis of the fabricated ring illustrated in FIGS. 6A-6F, according to one or more embodiments of the invention.
Figure 6H:
FIG. 6H illustrates a computer screenshot showing profile, positioning, power, and radius of the laser beam (units in mm) used for the Tracepro™ analysis in FIG. 6G, according to one or more embodiments of the invention.
Figure 6M:
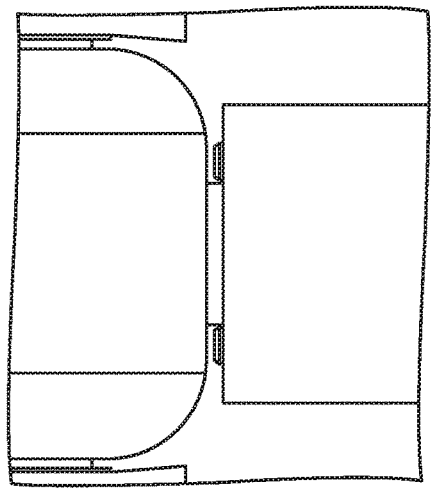
Figure 6J:
Figure 6L:
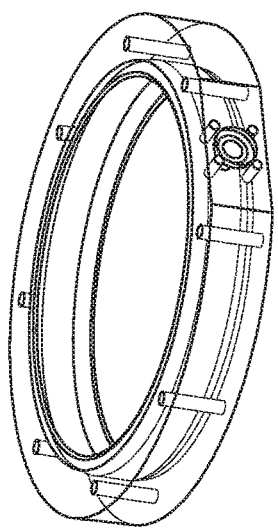
Figure 6I:
Figure 6K:
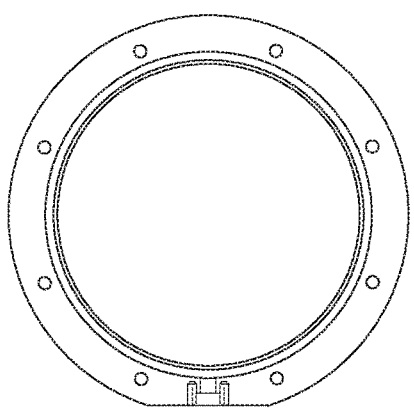

FIG. 6G shows a Tracepro™ optical analysis of the fabricated ring, showing intensity X as a percentage of the input intensity of the laser beam, and as a function of reflections in the cavity. In FIG. 6G, the laser beam makes 218 bounces between input and output from the cavity, corresponding to a path length of 33.22 meters, and the output intensity of the laser beam outputted from the cavity is 5% of the input intensity. For the Tracepro™ analysis of FIG. 6G, the window 616 is a ZnSe window, the inner surface of the ring has an IR gold coating, the laser is aligned such that an input angle of the laser beam 618 is 4 degrees with respect to the surface normal of the window, and the laser's output is positioned at a coordinate (−711.2 mm, 0, 20) where the origin is taken as the center of the ring (the distance of 711.2 mm or 28" is the value used for characterization of the cell in the lab), as shown in the screenshot of FIG. 6H. The window 616 in the cavity 600 is a window through which electromagnetic radiation 618 (or 212) can be inputted into the cavity 600 and through which electromagnetic radiation exits the cavity after a last pass of the electromagnetic radiation through the cavity (or through a sample if the cavity contains a sample).

For the embodiment illustrated in FIGS. 6A-F the calculated volume enclosed by the inner surface 602 of the cavity 600 is 789,855.56 $mm^3$ (according to Solidworks™), the ring 600 has a 6" inner diameter ID, a ~9.84" Outer Diameter (250 mm), ¾" flange through hole 604 diameter (×8), #10-32 tapped holes 606 for the window (×6), a 16 mm diameter, 20 mm deep window extrusion 608, an O-ring groove 716 for AS568A-011, and 40 mm cell height h.

FIGS. 6I-6M illustrate an embodiment of the ring that can be used in spaceflight, wherein the calculated volume enclosed by the inner surface 602 of the cavity 600 is 175,188.42 $mm^3$ (according to Solidworks™), the ring 600 has a 6" inner diameter ID, a ~7.086" Outer Diameter (180 mm), ¼-20" flange through hole 604 diameter (×8), #10-32 tapped holes 606 for the window (×4), a knife edge for a copper gasket, a cell lip over the inner diameter, a 16 mm diameter, 11 mm deep window extrusion 608, and 22 mm cell height h.

Figure 7A:
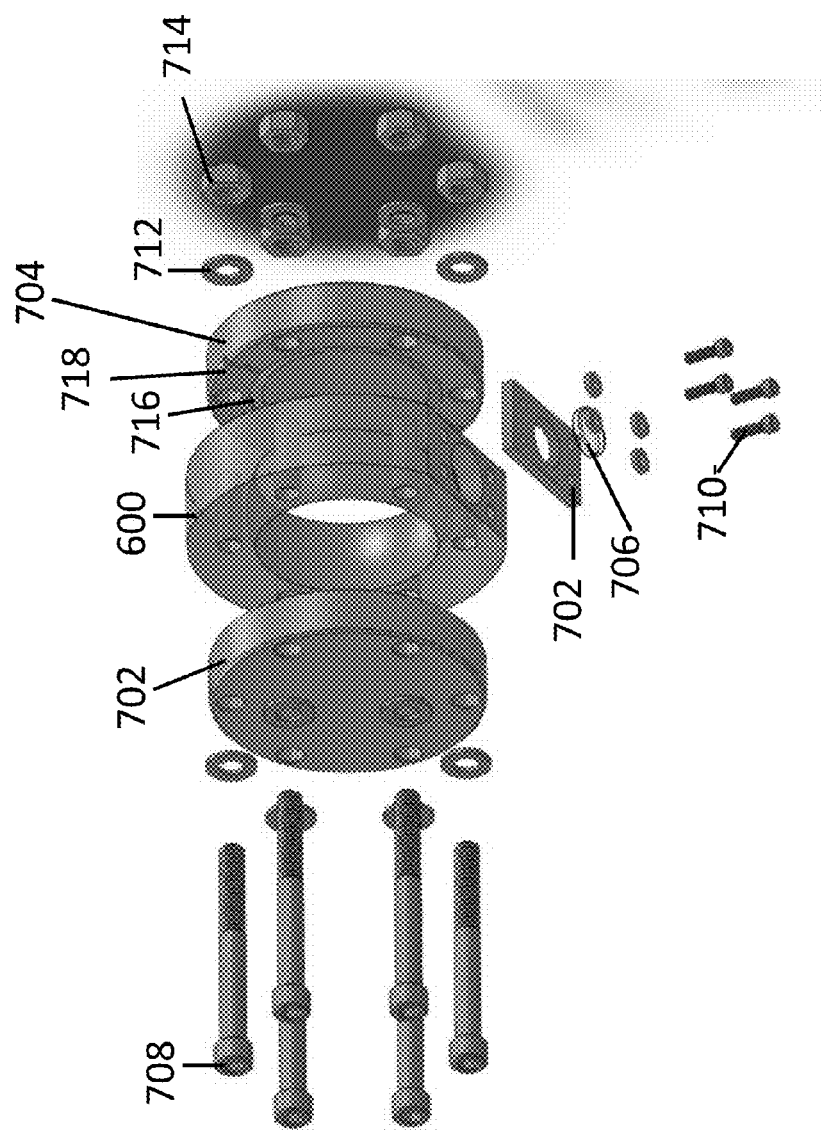
FIG. 7A illustrates an LSS assembly for testing of chemical detection signal levels in the Jet Propulsion Laboratory (JPL) Optical Metrology Laboratory.
Figure 7B:
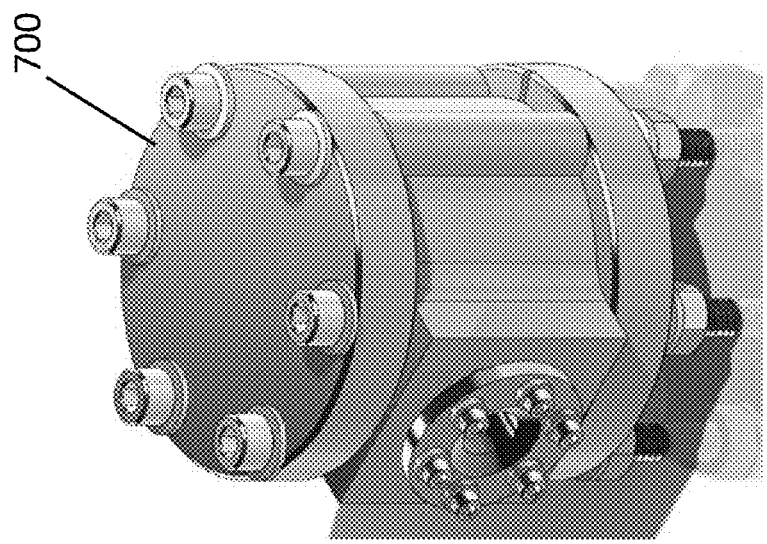
FIG. 7B illustrates the assembled LSS, according to one or more embodiments of the invention.

Block 510 represents further assembly. The step can include adding in all threaded inserts, assembling the calibration cell assembly (as illustrated in FIG. 7A) to obtain an assembled calibration cell 700 (as illustrated in FIG. 7B), and aligning all components (e.g., laser and detector). FIGS. 7A-7B illustrate a gas frequency reference cell comprising non-spherical ring 600, non-spherical face plate 702, non-spherical outer disk 704, window 706 with antireflective AR coating, bolts 708 for insertion in holes 604, bolts 710 for insertion in holes 606, washers 712, hex nuts 714 for fastening bolts 708, O-ring groove 716, and gasket 718. The cell can further comprise flanges. In one or more embodiments, a metrology laser system uses an acetylene gas frequency reference cell, wherein the all-metal non-spherical ring cavity 600 and cell 700 contain acetylene gas (e.g., for airborne applications).

Extra care must be taken with the inner surface 602 of the ring 600 to protect from scratching and contamination. The critical surfaces are the inner reflecting surface 602 and whatever surface the optics are mounted to. Secondarily, the laser injection hole 608 as well as top face 612 and bottom face 614, are critical because they must be sealed to prevent gas leakage.

The cell 700 can further comprise one or more sealable openings for inputting an analyte or sample into the cavity.

In one or more embodiments, the cavity has a height h in a range of 2 mm-20 mm, a width of 2 mm-60 mm, and a length of 2 mm-60 mm, and/or the cavity is dimensioned such that a volume of the cavity comprising the sample is between 33 $mm^3$ and 905000 $mm^3$. However, the dimensions can be scaled up or down. The ring 600 can have a height h as small as the laser beam (e.g., half a millimeter).

Figure 8:
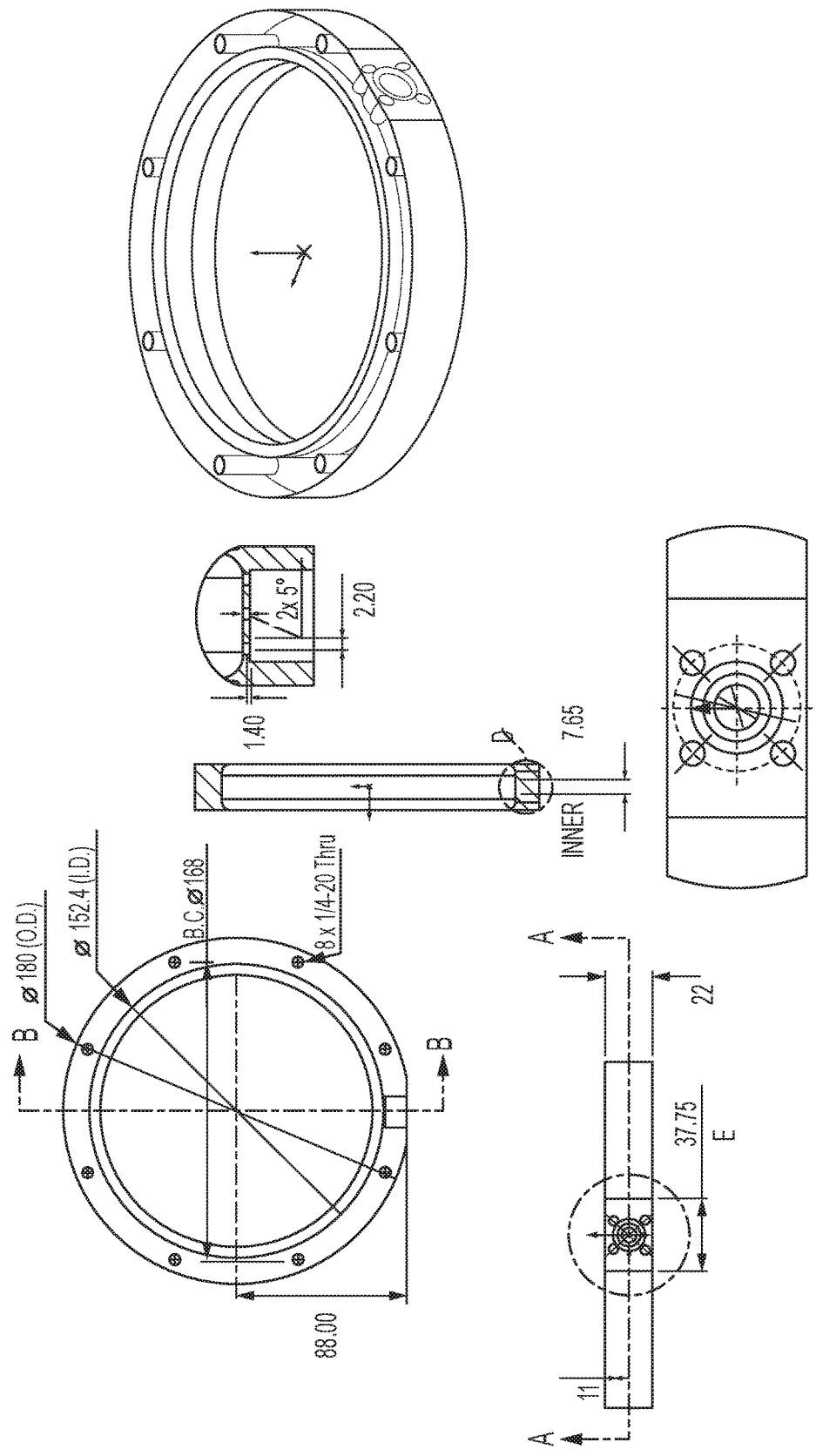
FIG. 8 illustrates specifications for a 6 inch Spherical Super Cell, according to one or more embodiments of the invention.

Different shapes for the inner surface and ring can be used. FIG. 8 illustrates an example comprising a 6 inch Spherical Super Cell.

The cavity or ring 600 can be fabricated from other materials such as pyrex or bulk metallic glass [8]. The cavity or ring can comprise or consist essentially of bulk metallic glass (BMG) or bulk metallic glass matrix composite (BMGMC). The inner reflecting surface 204, 602 can consist essentially of the BMG or BMGC or an optical coating can be applied to the BMG or BMGC surface. The BMG or BMGC ring or cavity can be fabricated by injection molding or casting, for example.

Laser Spider Web Sensor (LSS) Coupled to Portable Device

A portable laser system for use as a projector with iPhones or laptop computers can be used with a laser sensor according to one or more embodiments of the invention. The Microvision SHOWWX™ Laser Pico Projector (LPP) is an ideal platform for integration with the LSS.

In one or more embodiments, the laser intensity model for injection into the LSS coupled to the iPhone is that shown in FIG. 2 (wherein the intensity pattern is calculated using Tracepro optical ray trace software). However, the model of FIG. 3 could also be used. In one or more embodiments, the laser ring spectrometer geometry shown in FIG. 6A-6E can be designed to fit into Microvision© Laser Picoprojector (LPP) architecture for interface to mobile devices.

Figure 9:
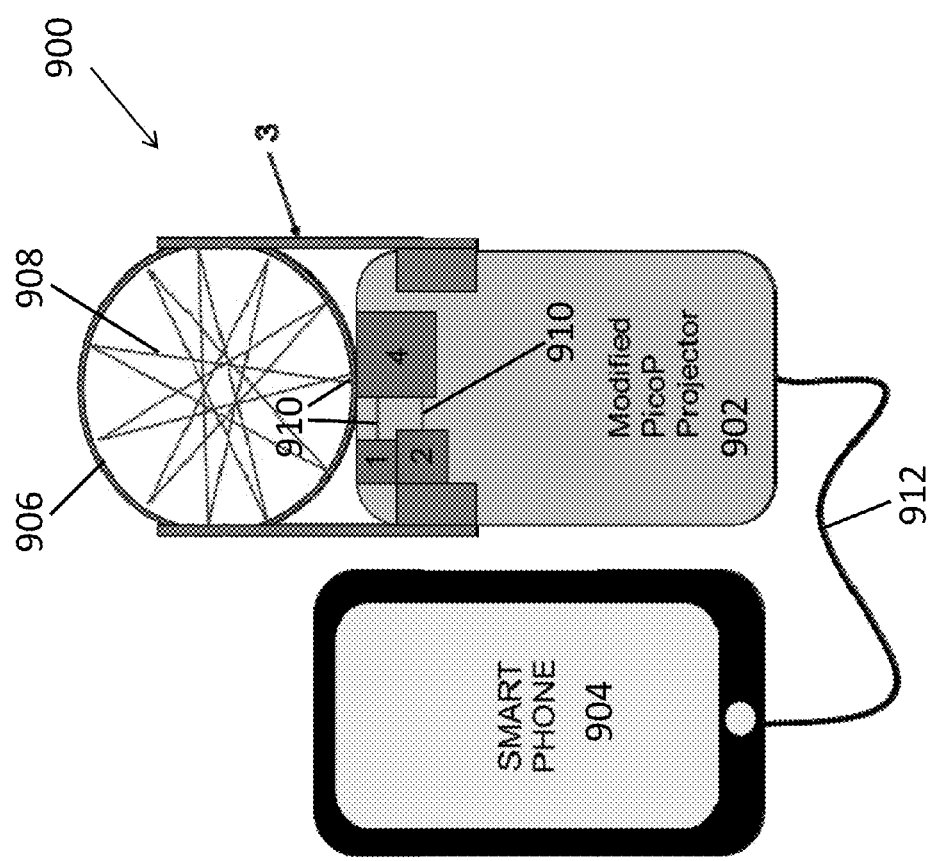
FIG. 9 illustrates an architecture for the LSS comprising a smart phone, wherein the showing a configuration wherein the LSS is integrated into a Modified PicoP projector according to one or more embodiments of the invention.

The LPP can be modified to connect directly to a portable device or smart phone. FIG. 9 shows an apparatus/package 900 comprising a modified pico projector 902 (e.g., modified picoP projector), wherein the modified pico projector 902 condenses a detector (e.g., diode detector such as Vigo model PV-4TE-10.6) 1, one or more lasers 2 (e.g., three lasers such as quantum cascade lasers, QCLs such as Alpes Lasers, models sbcw5701, sbcw2922 (1280.3 $cm^{-1}$), sbcw3055 (2205.4 $cm^{-1}$), and (1043.9 $cm^{-1}$), supporting optics bus 4, a laser controller, external interface (e.g., for communicating with the smart phone 904), and power source, into a handheld package 902. Thus, the modified picoprojector can comprise components 1, 2, 4, laser controller, external interface, and power source. The package 902 can further comprise the lasers (e.g., QCL) wired into the PicoP projector's amplifier and supporting electronics for the diode detector. The apparatus 900 further comprises ring cavity/multipass cell 906 (e.g., ring cavity 600) and LSS integration fixture 3 for attaching/coupling/mechanically interfacing the ring cavity/multipass cell 906 to the modified Pico projector 900.

In one or more embodiments, the cavity or ring 906 can further comprise top and bottom plates or attachments to sealably enclose the sample or analyte in the ring cavity 906/600. Moreover, the plates or attachments can further comprise one or more sealable openings for inputting the analyte or sample into the cavity 600/906. However, the ring 906 can be open on the top and/or bottom as illustrated in FIG. 9 to allow the ambient atmosphere to enter into the ring cavity 600/906 comprising the laser beam 908 for analysis.

The optics bus 4 can comprise an optical interfacing system (e.g. deformable mirror system) that injects or guides the laser beam 910 generated by laser 2 into the ring cavity at the appropriate angle to achieve the desired number of passes of the laser beam 908 in the cavity/multipass cell 600/906. Optical bus 4 can further guide the laser beam 910 that exits the ring cavity 600/906, after multiple passes through the cell 600/906, into the detector 1.

In one or more embodiments, the apparatus 900 has a height (H): 14 mm (0.55 in); width (W): 60 mm (2.36 in); length (L): 118 mm (4.64 in); weight: 122 g (4.3 oz); power: 400 mA 12 3.7 V (1.5 Watts); and battery life: 10 hours (e.g,. using Tekkeon MP1800 (4000 mAh 12 3.7V)).

The assembly/apparatus 900 can also be connected (e.g., via a wire 912 or wirelessly) to a smart phone 904. For example, the package 902 can comprise a Universal Serial Bus (USB) connection for connecting to the phone 904 or an antenna and supporting electronics for connecting to the phone 904 wirelessly (e.g., via WIFI or bluetooth or radio waves). In this way, absorption data (measured by the detector for the laser beam 908 transmitted through the sample in the cavity 600,906) can be transmitted/communicated to the smart phone 904 for spectral analysis and identification of the sample.

FIGS. 10A-10B illustrate a handheld detection system 1000 incorporating the apparatus 900 into a case like device 1002 which has the ability to house the phone 904 as well as the spectrometer system/apparatus 900. As shown in FIGS. 10A-10B, this system 1002 is only slightly larger than a smart phone 904 when closed (as shown in FIG. 10B) and is the size of a small book when opened (as shown in FIG. 10A) and in use. In this regard, the smart phone case 1002 comprises a first wing/section 1004 storing the smart phone 904; a second wing/section 1006 storing the portable spectrometer (package 902 and cavity 600/906); and a hinge or folding mechanism 1008 connecting the first wing 1004 to the second wing 1006, wherein the hinge/folding mechanism 1008 folds the smart phone case 1002 so that the second wing 1006 is superposed on the first wing 1004 when the smart phone case 1002 is closed.

FIG. 10B shows the case 1002 comprises an opening 1010 comprising the ring cavity 906/200 or housing/structure for holding/securing the ring cavity 906/200/600, an opening 1012 for housing the detector 1 and detector electronics, and an opening 1014 for housing the laser 2 and laser electronics.

Further openings for optical bus 4 and other interfacing electronics can also be provided in the case 1002. For example, the second wing/section 1006 can comprise a first opening 1010, hole, part, or attachment for holding the cavity 600/906, a second opening 1014, hole, part, or attachment for holding the source of electromagnetic radiation (e.g., laser 2 and laser controller), a third opening 1012, hole, part, or attachment for holding the detector 1 and supporting electronics, one or more additional openings through which the laser beam is transmitted to the cavity from the source and from the cavity to the detector, and one or more openings, parts or attachments for storing/holding an optical interfacing system 4, wherein the optical interfacing system guides the electromagnetic radiation into the cavity at an appropriate angle to achieve a desired number of the multiple passes, and guides the electromagnetic radiation after the number of passes onto the detector.

In one or more embodiments, the first wing has substantially a same surface area as the smart phone and the second wing has substantially a same size as the portable spectrometer. For example, when the smart phone case is closed, the smart phone case can have a length of 30 cm or less or 15 cm or less, a width of 30 cm or less or 15 cm or less, and a thickness of 4 cm or less. In one or more embodiments, the smart phone case is dimensioned such that a total volume occupied by the smart phone case including the phone and the portable spectrometer (package 902 and cavity 906) is no more than 15% larger than a volume occupied by the smart phone.

In one or more embodiments, the smart phone case can be fabricated from plastic, metal, BMG, or BMG composite, for example. In one or more embodiments, the ring and cell phone case assemblies are manufactured out of BMG or BMGMC by a molding process wherein the ring cavity is formed into the case 1002 (i.e., the cavity comprises a surface of the case 1002 shaped or molded to form a ring cavity including an inner reflecting surface 1016 (e.g., a molded surface shaped as surface 204 illustrated in FIG. 2) that reflects the electromagnetic radiation/laser beam 214 (e.g., as in FIG. 2) such that the electromagnetic radiation makes/forms multiple passes through the sample). In this way the ring cavity can be an integral part of the case 1002. Moreover, openings 1012, 1014, hinge 1008, and other housings for the support electronics, smart phone 904, and optics bus 4, as discussed above, can also be formed during the same molding process.

The handheld detection system design accounts for major system needs but specifics of each subsystem can also be implemented. In one or more embodiments, the system/apparatus 900/1000 can tailor the laser and optics subsystems for the specific detection of $CO_2$ or to fabricate a spectrometer allowing real-time analysis with unprecedented sensitivity for multiple target species enabling real time in situ validation for the OCO. The portable form factor makes the apparatus ideal for support of human space flight, the monitoring of crew cabin conditions, and for use in future planetary exploration missions, or medical applications, for example.

Hardware Environment

Figure 11:
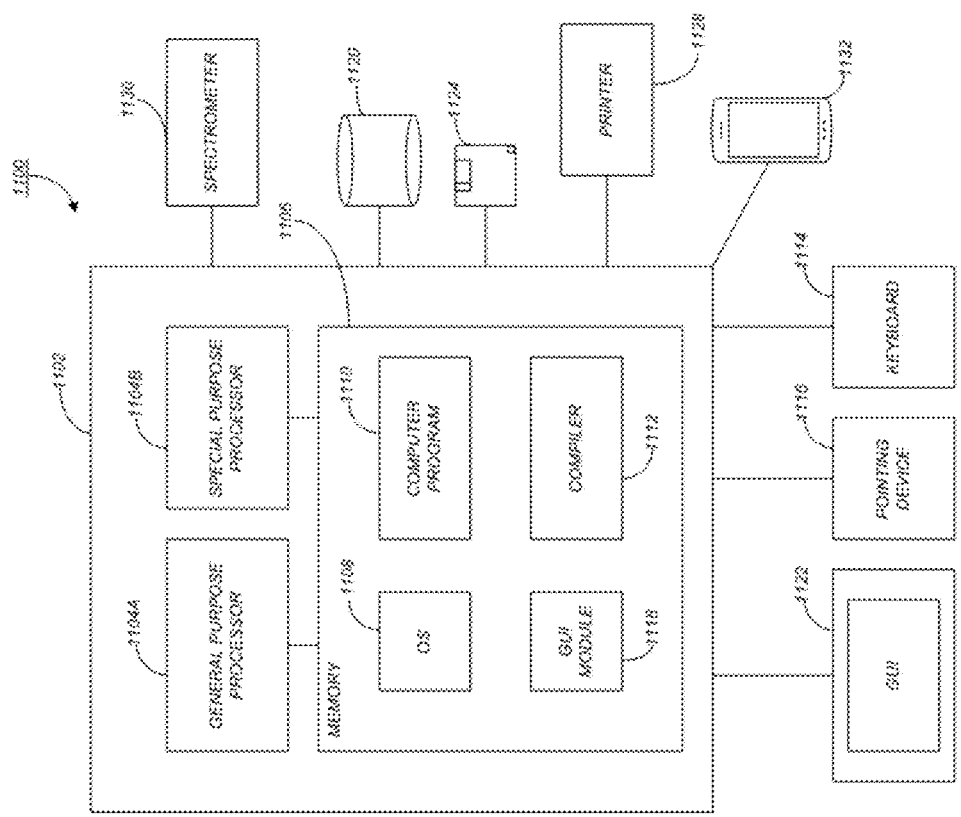
FIG. 11 is an exemplary hardware and software environment used to implement one or more embodiments of the invention.

FIG. 11 is an exemplary hardware and software environment 1100 used to implement one or more embodiments of the invention. The hardware and software environment includes a computer 1102 and may include peripherals. Computer 1102 may be a user/client computer, server computer, or may be a database computer. The computer 1102 comprises a general purpose hardware processor 1104A and/or a special purpose hardware processor 1104B (hereinafter alternatively collectively referred to as processor 1104) and a memory 1106, such as random access memory (RAM). The computer 1102 may be coupled to, and/or integrated with, other devices, including input/output (I/O) devices such as a keyboard 1114, a cursor control device 1116 (e.g., a mouse, a pointing device, pen and tablet, touch screen, multi-touch device, etc.) and a printer 1128. In one or more embodiments, computer 1102 may be coupled to, or may comprise, a portable or media viewing/listening device 1132 (e.g., an MP3 player, IPOD, NOOK, portable digital video player, cellular device, personal digital assistant, etc.). In yet another embodiment, the computer 1102 may comprise a multi-touch device, mobile phone, gaming system, internet enabled television, television set top box, or other internet enabled device executing on various platforms and operating systems.

In one embodiment, the computer 1102 operates by the general purpose processor 1104A performing instructions defined by the computer program 1110 under control of an operating system 1108. The computer program 1110 and/or the operating system 1108 may be stored in the memory 1106 and may interface with the user and/or other devices to accept input and commands and, based on such input and commands and the instructions defined by the computer program 1110 and operating system 1108, to provide output and results.

Output/results may be presented on the display 1122 or provided to another device for presentation or further processing or action. In one embodiment, the display 1122 comprises a liquid crystal display (LCD) having a plurality of separately addressable liquid crystals. Alternatively, the display 1122 may comprise a light emitting diode (LED) display having clusters of red, green and blue diodes driven together to form full-color pixels. Each liquid crystal or pixel of the display 1122 changes to an opaque or translucent state to form a part of the image on the display in response to the data or information generated by the processor 1104 from the application of the instructions of the computer program 1110 and/or operating system 1108 to the input and commands. The image may be provided through a graphical user interface (GUI) module 1118. Although the GUI module 1118 is depicted as a separate module, the instructions performing the GUI functions can be resident or distributed in the operating system 1108, the computer program 1110, or implemented with special purpose memory and processors.

In one or more embodiments, the display 1122 is integrated with/into the computer 1102 and comprises a multi-touch device having a touch sensing surface (e.g., track pod or touch screen) with the ability to recognize the presence of two or more points of contact with the surface. Examples of multi-touch devices include mobile devices (e.g., IPHONE, NEXUS S, DROID devices, etc.), tablet computers (e.g., IPAD, HP TOUCHPAD), portable/handheld game/music/video player/console devices (e.g., IPOD TOUCH, MP3 players, NINTENDO 3DS, PLAYSTATION PORTABLE, etc.), touch tables, and walls (e.g., where an image is projected through acrylic and/or glass, and the image is then backlit with LEDs).

Some or all of the operations performed by the computer 1102 according to the computer program 1110 instructions may be implemented in a special purpose processor 1104B. In this embodiment, the some or all of the computer program 1110 instructions may be implemented via firmware instructions stored in a read only memory (ROM), a programmable read only memory (PROM) or flash memory within the special purpose processor 1104B or in memory 1106. The special purpose processor 1104B may also be hardwired through circuit design to perform some or all of the operations to implement the present invention. Further, the special purpose processor 1104B may be a hybrid processor, which includes dedicated circuitry for performing a subset of functions, and other circuits for performing more general functions such as responding to computer program 1110 instructions. In one embodiment, the special purpose processor 1104B is an application specific integrated circuit (ASIC).

The computer 1102 may also implement a compiler 1112 that allows an application or computer program 1110 written in a programming language such as C, C++, Assembly, SQL, PYTHON, PROLOG, MATLAB, RUBY, RAILS, HASKELL, or other language to be translated into processor 1104 readable code. Alternatively, the compiler 1112 may be an interpreter that executes instructions/source code directly, translates source code into an intermediate representation that is executed, or that executes stored precompiled code. Such source code may be written in a variety of programming languages such as JAVA, JAVASCRIPT, PERL, BASIC, etc. After completion, the application or computer program 1110 accesses and manipulates data accepted from I/O devices and stored in the memory 1106 of the computer 1102 using the relationships and logic that were generated using the compiler 1112.

The computer 1102 also optionally comprises an external communication device such as a modem, satellite link, Ethernet card, or other device for accepting input from, and providing output to, other computers 1102.

In one embodiment, instructions implementing the operating system 1108, the computer program 1110, and the compiler 1112 are tangibly embodied in a non-transitory computer-readable medium, e.g., data storage device 1120, which could include one or more fixed or removable data storage devices, such as a zip drive, floppy disc drive 1124, hard drive, CD-ROM drive, tape drive, etc. Further, the operating system 1108 and the computer program 1110 are comprised of computer program 1110 instructions which, when accessed, read and executed by the computer 1102, cause the computer 1102 to perform the steps necessary to implement and/or use the present invention or to load the program of instructions into a memory 1106, thus creating a special purpose data structure causing the computer 1102 to operate as a specially programmed computer executing the method steps described herein (e.g., the spectral analysis of the absorption spectrum measured by the portable spectrometer 1130). Computer program 1110 and/or operating instructions may also be tangibly embodied in memory 1106 and/or portable spectrometer 1130, thereby making a computer program product or article of manufacture according to the invention. As such, the terms "article of manufacture," "program storage device," and "computer program product," as used herein, are intended to encompass a computer program accessible from any computer readable device or media.

The computer 1102 can be stored in a smart phone case 1002 or computer case/enclosure and connected to the portable spectrometer 1130 (e.g., as illustrated in FIGS. 2 and 10A-10B). In one or more embodiments, the portable spectrometer 1130 includes a cavity 600 into which a sample is placed; a source (e.g., including laser 2, laser controller/support electronics (e.g., for the laser), and/or optics bus 4) for emitting electromagnetic radiation that is directed on the sample in the cavity 600, wherein the electromagnetic radiation is reflected within the cavity 600 to form multiple passes of the electromagnetic radiation through the sample; a detector (e.g,. detector 1 and/or support electronics (e.g,. for the detector)) for detecting the electromagnetic radiation after the electromagnetic radiation has interacted with the sample in the cavity, the detector outputting a signal/data stream in response to the detecting; and a device 1202 for (e.g., digitally) communicating the (e.g,. digital) signal/data stream to a smart phone or computer 1102, wherein the smart phone/computer 1102 executes an application or program 1110 that performs a spectral analysis of the signal. In one or more embodiments, the portable spectrometer 1130 comprises the computer 1130 or the computer 1130 is integrated into the portable spectrometer 1130 as one or more processors or chips configured to perform one or more functions (e.g., spectral analysis of the absorption spectrum, wirelessly transmit the data from the detector 1 to another computer). The computer case or smart phone case can store the portable spectrometer 1130.

Of course, those skilled in the art will recognize that any combination of the above components, or any number of different components, peripherals, and other devices, may be used with the computer 1102.

Figure 12:
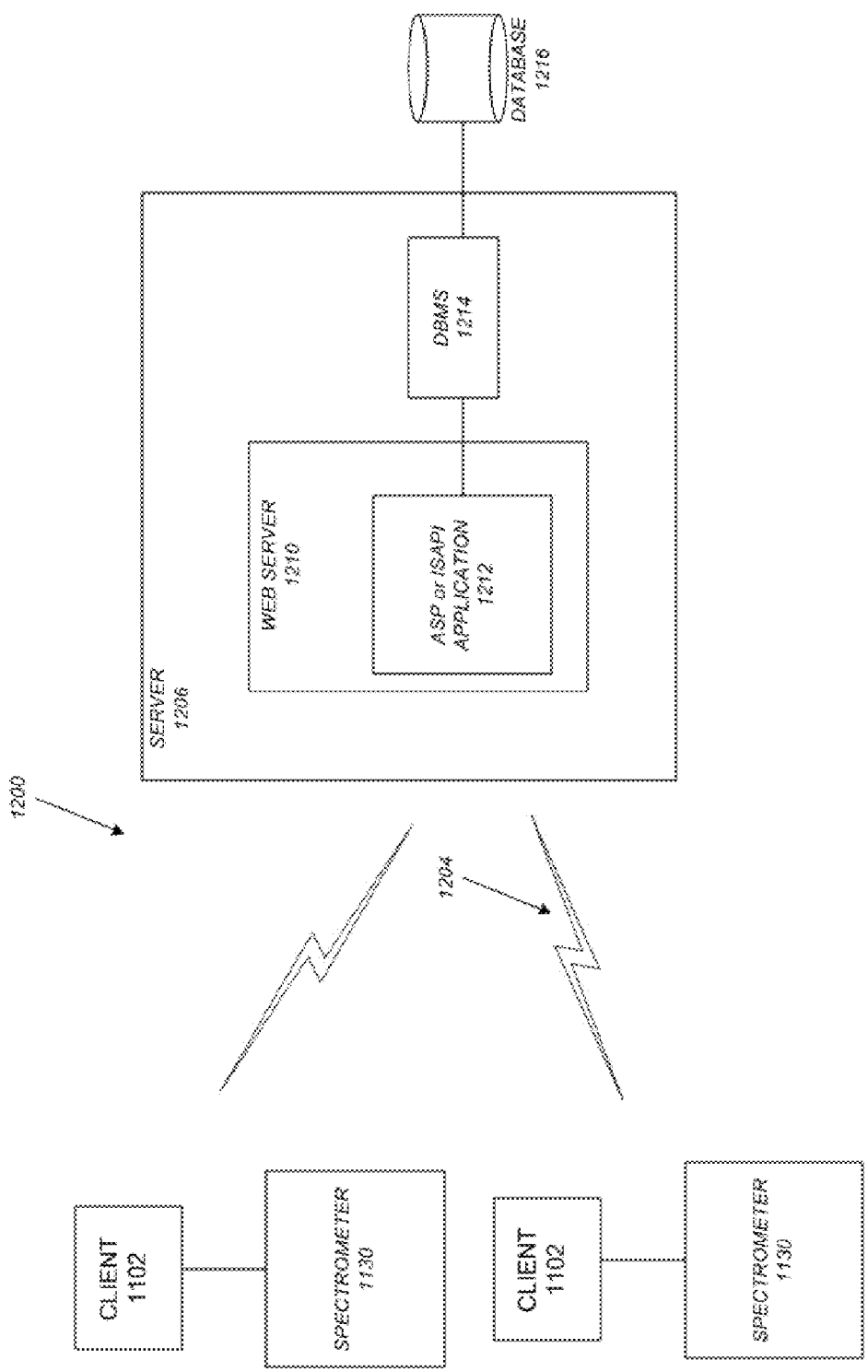
FIG. 12 schematically illustrates a typical distributed/cloud-based computer system using a network to connect client computers to server computers, according to one or more embodiments of the invention.

FIG. 12 schematically illustrates a typical distributed/cloud-based computer system 1200 using a network 1204 to connect client computers 1202 to server computers 1206. A typical combination of resources may include a network 1204 comprising the Internet, LANs (local area networks), WANs (wide area networks), SNA (systems network architecture) networks, or the like, clients 1202 that are personal computers or workstations (as set forth in FIG. 11), and servers 1206 that are personal computers, workstations, minicomputers, or mainframes (as set forth in FIG. 11). However, it may be noted that different networks such as a cellular network (e.g., GSM [global system for mobile communications] or otherwise), a satellite based network, or any other type of network may be used to connect clients 1202 and servers 1206 in accordance with embodiments of the invention.

A network 1204 such as the Internet connects clients 1202 to server computers 1206. Network 1204 may utilize ethernet, coaxial cable, wireless communications, radio frequency (RF), etc. to connect and provide the communication between clients 1202 and servers 1206. Further, in a cloud-based computing system, resources (e.g., storage, processors, applications, memory, infrastructure, etc.) in clients 1202 and server computers 1206 may be shared by clients 1202, server computers 1206, and users across one or more networks. Resources may be shared by multiple users and can be dynamically reallocated per demand. In this regard, cloud computing may be referred to as a model for enabling access to a shared pool of configurable computing resources.

Clients 1202 may execute a client application or web browser and communicate with server computers 1206 executing web servers 1210. Such a web browser is typically a program such as MICROSOFT INTERNET EXPLORER, MOZILLA FIREFOX, OPERA, APPLE SAFARI, GOOGLE CHROME, etc. Further, the software executing on clients 1202 may be downloaded from server computer 1206 to client computers 1202 and installed as a plug-in or ACTIVEX control of a web browser. Accordingly, clients 1202 may utilize ACTIVEX components/component object model (COM) or distributed COM (DCOM) components to provide a user interface on a display of client 1202. The web server 1210 is typically a program such as MICROSOFT'S INTERNET INFORMATION SERVER.

Web server 1210 may host an Active Server Page (ASP) or Internet Server Application Programming Interface (ISAPI) application 1212, which may be executing scripts. The scripts invoke objects that execute business logic (referred to as business objects). The business objects then manipulate data in database 1216 through a database management system (DBMS) 1214. Alternatively, database 1216 may be part of, or connected directly to, client 1202 instead of communicating/obtaining the information from database 1216 across network 1204. When a developer encapsulates the business functionality into objects, the system may be referred to as a component object model (COM) system. Accordingly, the scripts executing on web server 1210 (and/or application 1212) invoke COM objects that implement the business logic. Further, server 1206 may utilize MICROSOFT'S TRANSACTION SERVER (MTS) to access required data stored in database 1216 via an interface such as ADO (Active Data Objects), OLE DB (Object Linking and Embedding DataBase), or ODBC (Open DataBase Connectivity).

Generally, these components 1200-1216 all comprise logic and/or data that is embodied in/or retrievable from device, medium, signal, or carrier, e.g., a data storage device, a data communications device, a remote computer or device coupled to the computer via a network or via another data communications device, etc. Moreover, this logic and/or data, when read, executed, and/or interpreted, results in the steps necessary to implement and/or use the present invention being performed.

Although the terms "user computer", "client computer", and/or "server computer" are referred to herein, it is understood that such computers 1202 and 1206 may be interchangeable and may further include thin client devices with limited or full processing capabilities, portable devices such as cell phones, notebook computers, pocket computers, multi-touch devices, and/or any other devices with suitable processing, communication, and input/output capability.

Embodiments of the invention are implemented as a software application on a client 1202 or server computer 1206. Further, as described above, the client 1202 or server computer 1206 may comprise a thin client device or a portable device that has a multi-touch-based display.

Of course, those skilled in the art will recognize that any combination of the above components, or any number of different components, peripherals, and other devices, may be used with computers 1202 and 1206.

Figure 13:
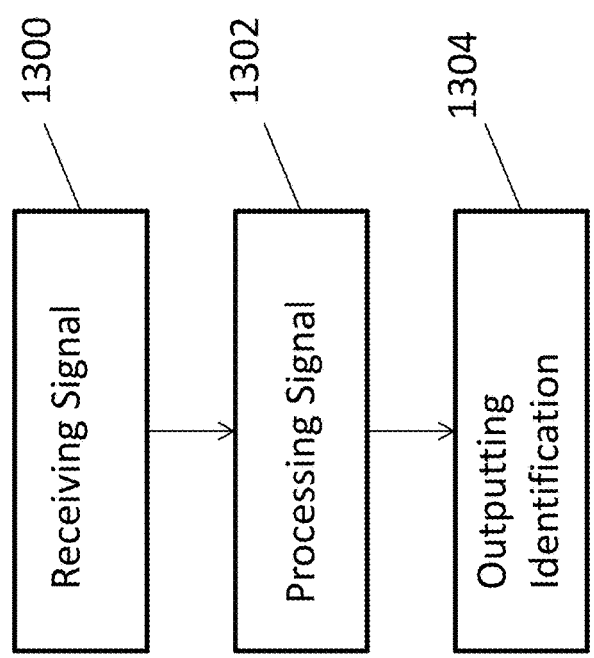
FIG. 13 is a flowchart illustrating a method of processing a signal according to one or more embodiments of the invention.

FIG. 13 is a flowchart illustrating a method of processing the signal using the computer 1102.

Block 1300 represents receiving, in the computer 1102, the signal/data (e.g., absorption as a function of frequency of the laser beam 908, 216) from the detector 208 in the portable spectrometer 1130 of FIG. 2 or FIGS. 9-10, when the cavity 200, 600 comprises a sample. One or more processors or chips/devices can be configured and included in the spectrometer to wirelessly transmit the data to a computer 1102.

Block 1302 represents processing the signal/data to identify the sample. The step can comprise comparing the absorption spectrum of the laser beam 216 with the absorption features of known compounds/species/elements, as illustrated in FIG. 1. The step can comprise comparing an amount of absorption of the laser beam 216 at a given frequency with an amount of absorption at the given frequency for a known chemical species. If the absorption spectrum or amount of absorption of the laser beam 216 matches that of the known species, the sample in the cavity can be identified by the processor as comprising that known species.

Block 1304 represents outputting, from the computer 1102, an identification of the sample (e.g., as a graphical output on the display 1122 or using a voice signal, for example).

Molding Process Fabricating The Ring Cavity And/Or Casing

Figure 14:
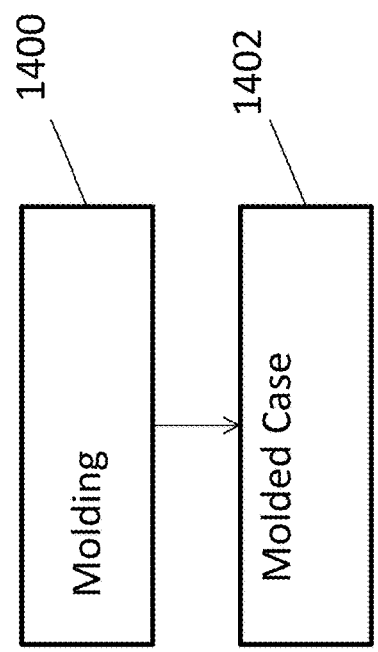
FIG. 14 illustrates a method of molding a smart phone case according to one or more embodiments of the invention.

FIG. 14 illustrates a method of fabricating a smart phone/computer case/spectrometer case.

Block 1400 represents molding a material (e.g., plastic, BMG, BMGMC), using the mold, into a smart phone case or computer case wherein the smart phone case/computer case is capable of holding a smart phone/computer and the portable spectrometer. The molding can comprise die casting or injection molding, for example. The mold can include portions/parts capable of molding attachment(s), mount(s), accessories, holes, openings, screw holes, or other features capable of holding the portable spectrometer (including the cavity, the laser, the detector, and power source). The mold can be designed to mold the case 1002 illustrated in FIG. 10A-10B, for example.

Block 1402 represents the end result, a smart phone or portable computer case molded to hold a smart phone or portable computer and portable spectrometer.

The molding of Block 1400 forms the case that holds the portable spectrometer such that the cavity, the source (e.g., laser), and the detector are operably coupled during operation of the spectrometer—i.e., the case holds the cavity and the source such that the electromagnetic radiation emitted and directed from the source is reflected within the cavity to form multiple passes of the electromagnetic radiation through a sample in the cavity. Moreover, the case can hold the detector such that the detector detects the electromagnetic radiation after the multiple passes and outputs a signal that can be spectrally analyzed (by the smart phone or computer) to identify the sample.

In one or more embodiments, the smart phone/computer case can include additional features/components to secure the source, cavity, and detector (e.g., adhesive, screws, etc) during operation of the spectrometer. In one or more embodiments, the computer can comprise a chip/processor/integrated circuit held in the case.

Manufacturing Using Bulk Metallic Glass (BMG) and Bulk Metallic Glass Matrix Composite (BMGMC)

Die-casting BMGs or BMGMCs from a liquid state can be used to fabricate the ring cavity 200/906 and/or smart phone case 1002 (or portable computer case). The technique involves heating the liquid BMG or BMGMC up in a crucible (through radio frequency (RF) heating, resistance heating, oven heating, etc.) and then injecting the liquid into a mold using a shot-sleeve and die under typically tens of tons of force. The high processing temperature of the liquid and the extreme forces used in casting allow for extremely complex molds to be filled using the process. By reducing the flow velocity (to limit turbulence), or by using a counter-gravity casting variant, parts with mirror finishes can be replicated using the processes. This can be done by fabricating a mirror-polished piece of steel or carbide and then die-casting BMGs over the mold at high pressure and low flow velocity. With the correct application of temperature and pressure, a one-step process can be used to fabricate an optical finish. However, an optical coating can also be applied if desired.

Figure 15:
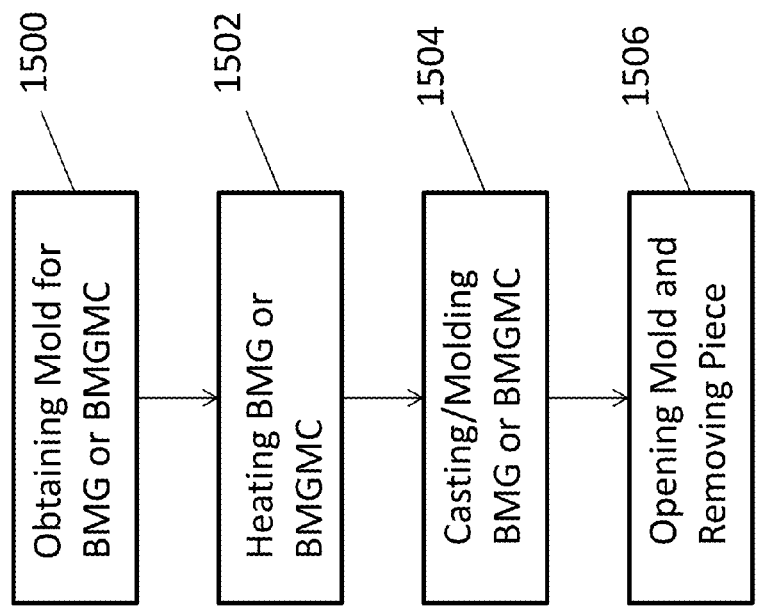
FIG. 15 illustrates a method of molding the ring cavity and/or spectrometer case using bulk metallic glass, according to one or more embodiments of the invention.

FIG. 15 is a flowchart illustrating a method of fabricating a ring cavity and/or portable spectrometer case from BMG or BMGMC materials using die casting or injection molding.

Figure 16:
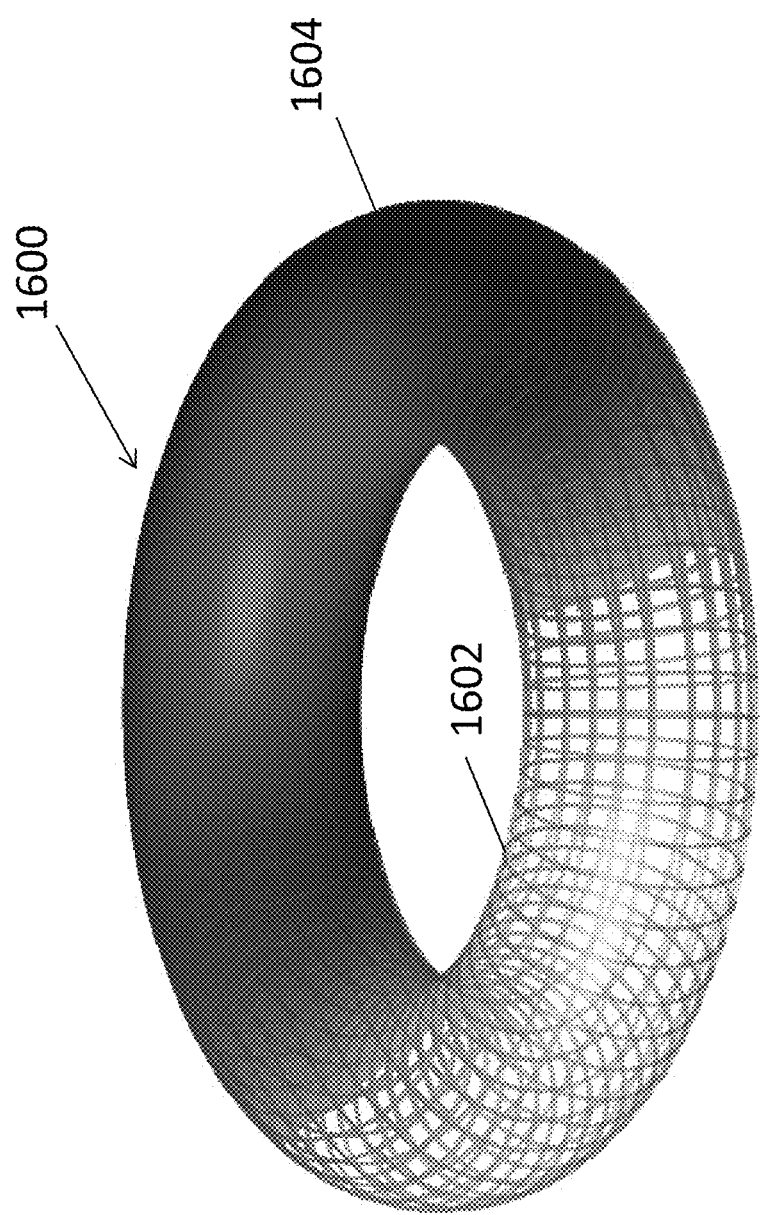
FIG. 16 illustrates a toroidal mold that can be used to mold a BMG ring cavity according to one or more embodiments of the invention.

Block 1500 represents obtaining, designing, and/or fabricating a mold. The mold part for molding the ring cavity can comprise a surface that is the negative of the inner reflective surface (e.g., 204 in FIG. 2 or 1016 in FIG. 10A) of the ring cavity (e.g., 200 in FIG. 2), so that once removed from the mold, the inner reflective surface 204/1016 has the desired (e.g., elliptical) shape. For example, the mold can comprise a torus, elliptic torus, 1600 or toroidal/doughnut shaped mold having a cross-section that is an ellipse 1602, as illustrated in FIG. 16. The torus can be fabricated from steel or carbide, for example, and have a smooth mirror polished outer surface 1604 so that casting of the BMG or BMGMC over the outer surface 1604 of the mold forms an optically finished mirror surface 1016/204 of a BMG/BMGMC ring cavity part. Furthermore, the torus shaped mold having the mirrored outer surface can comprise a multi-component piece so that the mold can also be broken apart or disassembled (e.g., using hydraulics) after the mirror surface 204/1016 is cast, thereby allowing easy removal of the mold from the BMG/BMGMC mirror surface 204/1016 while preventing damage to the mirror surface 204/1016 (the disassembly prevents trapping of the BMG or BMGMC material on the mold).

A mold part can also be designed to mold the BMGMC or BMG to form the case (e.g., 1002 in FIG. 10A) including attachments, housings, mount(s), accessories, holes, openings (e.g., 1012, 1014), screw holes, or other features capable of holding the smart phone and portable spectrometer (including the cavity, the laser, the detector, power source, support electronics, and optics bus), as well as hinge 1008, as illustrated in FIG. 10A-10B. Thus, the mold can comprise multi-component pieces for molding the mirror surface 204 of the ring cavity as well as mold part(s) for molding the case 1002.

Block 1502 represents heating a BMG or BMGMC ingot to above the liquidus to form a BMG or BMGMC liquid. The BMG or BMGMC can be heated in a crucible, for example.

Block 1504 represents casting or molding the heated and liquid BMG or BMGMC. The step can comprise injecting the BMG or BMGMC liquid into the mold obtained in Block 1400 (e.g., the multi-component toroidal piece and/or the mold part for the case 1002) under pressure. The BMG or BMGMC liquid can be injected or cast into the mold using a plunger or other external force (including counter gravity). The step can comprise pressing the heated liquid BMGMC or BMG into the mold from a shot-sleeve, at a die-casting pressure between 0.1-200 tons, at a processing a temperature between 600-1500° C., and at a flow velocity of the liquid into the molds that is laminar. The inlet for injecting or introducing the BMG or BMGMC into the mold can be placed so as to not interfere with the mirror surface. The molds are massive and act as a thermal heat sink for the alloy, which allows vitrification.

Block 1506 represents, after the casting/molding, opening the mold and removing the molded piece comprising the ring cavity 200, or the case 1002 comprising the ring cavity having inner surface 1016 integrated into the case 1002. The opening of the mold can comprise disassembling the multi-component torus/toroidal piece to allow easy removal of the mold from the mirror surface 204/1016, thereby preventing damage to the mirror surface 204/1016. An injection system can also be used to remove the finished part to reduce damage to the finished part. The torus/toroid/mold can be disassembled such that it can also be reassembled (e.g., using hydraulics) for reuse in another ring cavity casting process.

The end result is a ring cavity and/or smart phone case comprising or consisting essentially of bulk metallic glass or bulk metallic glass matrix composite. In one or more embodiments where the molding monolithically integrates the ring cavity with the smart phone case, the cavity comprises/is defined by a molded surface of the smart phone case (comprising or consisting essentially of BMG/BMG composite) such that the electromagnetic radiation emitted and directed from the laser can be reflected from the molded surface to form the multiple passes of the electromagnetic radiation through the sample in the cavity during operation of the portable spectrometer. Specifically, the molded surface is of sufficient quality such that the signal, outputted by the detector in response to detecting the electromagnetic radiation after the multiple passes reflected from the molded surface, can be spectrally analyzed (by the smart phone or computer) to identify the sample.

Thus, Blocks 1400-1402 and 1500-1506 illustrate how the cavity can be formed to comprise a molded surface of the smart phone case, wherein the electromagnetic radiation can be reflected from the molded surface to form the multiple passes of the electromagnetic radiation through the sample.

Thus, Blocks 1400-1402 and 1500-1506 illustrate molding a material into a smart phone case wherein the smart phone case is capable of holding a smart phone and a portable spectrometer, the portable spectrometer including a cavity; a source for emitting electromagnetic radiation that is directed on the sample in the cavity, wherein the electromagnetic radiation is reflected within the cavity to form multiple passes of the electromagnetic radiation through the sample; and a detector for detecting the electromagnetic radiation after the electromagnetic radiation has made the multiple passes through the sample in the cavity, the detector outputting a signal in response to the detecting and communicating the signal to the smart phone, and the smart phone executing an application that performs a spectral analysis of the signal.

Advantages and Improvements

Diode lasers are a technology that has allowed relatively easy access to the molecular fingerprint region of the infrared spectrum. They are robust monopolar semiconductor laser devices that can be fabricated to operate at specific wavelengths virtually anywhere in the 2- to 20-micron range. The Herriott cell used in these sensors has evolved from designs flown on the U-2 spy plane [3], Unmanned Aerial Vehicle (UAVs) [4], and planetary probes [5]. Light is passed into the cell through a hole in one mirror, which is then bounced multiple times between the mirrors, to finally exit at the same hole through which it entered, but at a complimentary angle. There are several different configurations for Herriott cells depending on the relationship between the curvature of the mirrors and their separation, resulting in different bounce patterns or geometric modes. The chosen mode of the Herriott cells currently in use is the C-3 mode, as this affords stability against lateral movement of the mirrors with respect to one another. Research into alternative configurations for these optical systems has led to a spherical ring design for the absorption cell. Using a spherical ring design enables the facile integration of these systems into common air intake and exhaust systems. Other benefits of this new design allows for higher laser path length per absorption volume ratios, allowing for a greater sensitivity in detection for a given volume. The monolithic nature of the new absorption ring design allows for alignment stability for a wide range of vibrational and thermal changes, making it ideal for handheld and field deployable gas detection.

In particular the integration of the ring design into the exhaust systems of vehicles, trucks, busses, trains, ships, factories, and power plants will allow efficient real time monitoring of green house chemicals. Using either a hard line or wireless interface, data from these detectors can be easily collected and processed to better understand the concentrations, sources and sinks of greenhouse gasses. Aside from the environmental benefits of a multi spectrum trace gas detection system, air quality monitoring in both business and residential buildings could be used to improve the general health of the inhabitants. Spectrometers could be used to monitor $CO_2$, CO, $O_2$ and humidity levels by integrating the spherical ring designs into existing heating, ventilating, and air conditioning (HVAC) systems, the detection capability could be easily installed maintained.

Thus, one or more embodiments of the new technology developed at the Jet Propulsion Laboratory now enables real time in situ measurements of key chemicals important in global climate change including $CO_2$, $N_2O$, $CH_4$, CO, $H_2O$, and many other species of interest. Emergence of mobile smart phone technology presents an ideal opportunity to deploy multiple ($>1.0\times10^9$) sensors around the globe and form a network of in situ sensors to help map out sources and sinks of $CO_2$ and other important greenhouse gases. A network of sensors on land, ships, and aircraft would provide needed verification and validation for the Orbiting Carbon Observatory 2 (OCO-2) [1]. FIG. 12 shows a network of portable spectrometers 1130 in communication with a server.

The spectrometer according to one or more embodiments of the invention can also be used in medical applications, e.g., to identify biomarkers or disease markers in exhaled breath/breath condensate such as nitric oxide, carbon monoxide, and volatile organic compounds or other species identified by canines as being related to disease. Such breath markers can be used to measure hypoxia, oxidative stress, and inflammation in a spectrum of clinical conditions ranging from asthma, cancer, heart disease, transplant rejection (e.g., lung allograft rejection), for example.

REFERENCES

The following references are incorporated by reference herein.

[1] Website having home page identified as "http://oco.jpl.nasa.gov/" on the information disclosure statement submitted on Sep. 24, 2015.

[2] "Measurement of Broad Absorption Features Using a Tunable External Cavity Quantum Cascade Laser," M. C. Phillips, T. L. Myers, M. D. Wojcik, M. S. Taubman, B. D. Cannon, and D. C. Scott, Proc. SPIE Int. Soc. Opt. Eng. 6760, 676003 (2007).

[3] "Aircraft (ER-2) Laser Infrared Absorption Spectrometer (ALIAS) for In-situ Stratospheric Measurements of HCl, $N_2O$, $CH_4$, $NO_2$, and $HNO_3$", C. R. Webster, R. D. May, C. A. Trimble, R. G. Chave and J. Kendall, *Applied Optics*, 33, 454-472, (1994).

[4] "Airborne Laser Infrared Absorption Spectrometer (ALIAS-II) for in situ atmospheric measurements of $N_2O$, $CH_4$, CO, HCl, and $NO_2$ from balloon or remotely piloted aircraft platforms," D. C. Scott, R. L. Herman, C. R. Webster, R. D. May, G. J. Flesch, and E. J. Moyer, Applied Optics, 38, 4609-4622 (1999).

[5] "Multilaser Herriott cell for planetary tunable laser spectrometers," C. G. Tarsitano and C. R. Webster, Applied Optics, 46, 6923-6935 (2007).

[6] Disease Markers in Exhaled-Breath, edited by Nandor Marczin, Sergei Kharitonov, Sir Magdi Yacoub, and Peter J. Barnes, CRC Press (2002), ISBN 9780203909195—CAT# HE00047.

[7] Website identified as "http://pinestreetfoundation.org/research/canine/" listed on the information disclosure statement submitted on Sep. 24, 2015.

[8] Designing metallic glass matrix composites with high toughness and tensile ductility Douglas C. Hofmann et. al Vol 45, 28 Feb. 2008, nature, doi:10.1038/nature06598.

[12] U.S. Patent Publication No. 20130139964 by Hofmann et. al. entitled "Amorphous metals and composites as mirrors and mirror assemblies."

[13] S. M. Chernin, "New generation of multipass systems in high resolution spectroscopy," Spectrochimica Acta Part A, 52, 1009-1022 (1996).

[14] S. M. Chernin, "Multipass annular mirror system for spectroscopic studies in shock tubes," Journal of Modern Optics, Vol. 51, No. 2. 223-231, 20 Jan. 2004.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:
1. A portable spectrometer, comprising:
a smart phone case or portable computer case holding a portable spectrometer, wherein the portable spectrometer includes:

a cavity;
a laser source for emitting electromagnetic radiation that is directed on a sample in the cavity, wherein the electromagnetic radiation is reflected within the cavity to form multiple passes of the electromagnetic radiation through the sample; and
a detector for detecting the electromagnetic radiation after the electromagnetic radiation has made the multiple passes through the sample in the cavity, the detector outputting a signal in response to the detecting and communicating the signal to a smart phone or portable computer, and the smart phone or portable computer executing an application that performs a spectral analysis of the signal; and
wherein the smart phone case or the portable computer case further comprises a first opening comprising the cavity, a second opening holding the laser, and a third opening holding the detector.

2. The portable spectrometer of claim 1, wherein the cavity includes a ring having an elliptical inner surface.

3. The portable spectrometer of claim 1, wherein:
the cavity includes an inner surface substantially described by the equation:

$$\frac{x^2 + y^2}{a^2} + \frac{z^2}{c^2} = 1,$$

wherein:
x, y, and z are Cartesian coordinates,
a is an equatorial radius comprising a maximum value of x and y,
c is a distance along the z- axis from coordinate (x=0, y=0, z=0) to a pole of the spheroid described by the equation, and
a ≠ c,
the electromagnetic radiation incident on the inner surface is reflected from multiple regions of the inner surface such that the multiple passes of the electromagnetic radiation through the sample in the cavity are formed, and
one or more processors in the smart phone form an output identifying a composition of the sample.

4. The spectrometer of claim 3, wherein z<c.

5. The spectrometer of claim 3, wherein:
z is in a range of 2 mm-20 mm, and
a is in a range of 2 mm-60 mm.

6. The spectrometer of claim 3, wherein:
an angle of incidence of the electromagnetic radiation, at a first reflection within the cavity, is between more than 0 degrees and 45 degrees,
a is less than 60 mm,
z is less than 20 mm, and
the angle of incidence, a, and z are such that a total path length of the electromagnetic radiation transmitted through the sample includes a distance of 30 meters.

7. The spectrometer of claim 3, wherein an angle of incidence of the electromagnetic radiation at a first reflection within the cavity, a, and z are selected such that the spectrometer can identify the sample having a relative concentration in the cavity of 50 parts-per-billion by volume (ppbv).

8. The spectrometer of claim 1, further comprising:
one or more windows in the cavity through which the electromagnetic radiation is inputted into the cavity and through which the electromagnetic radiation exits the cavity after a last pass of the electromagnetic radiation through the sample, the detector positioned to receive the electromagnetic radiation after the last pass.

9. The spectrometer of claim 1, wherein the cavity is dimensioned such that a volume of the cavity comprising the sample is between 33 $mm^3$ and 905000 $mm^3$.

10. The portable spectrometer of claim 1, wherein the smart phone case further comprises:
a first wing for storing the smart phone;
a second wing comprising the first opening, the second opening, and the third opening; and
a hinge connecting the first wing to the second wing, wherein the hinge folds the smart phone case so that the second wing is superposed on the first wing when the smart phone case is closed.

11. The portable spectrometer of claim 10, wherein the first wing has substantially a same surface area as the smart phone and the second wing has substantially a same size as the portable spectrometer.

12. The portable spectrometer of claim 10, wherein, when the smart phone case is closed, the smart phone case has a length of 15 cm or less, a width of 15 cm or less, and a thickness of 4 cm or less.

13. The portable spectrometer of claim 10, wherein the second wing comprises
the first opening holding the cavity, and
one or more additional openings through which the laser beam is transmitted to the cavity from the laser and from the cavity to the detector.

14. The spectrometer of claim 1, wherein:
the portable spectrometer further comprises an optical interfacing system, and
the optical interfacing system:
guides the electromagnetic radiation into the cavity at an appropriate angle to achieve a desired number of the multiple passes,
guides the electromagnetic radiation after the number of passes onto the detector, and
is stored in the smart phone case.

15. The spectrometer of claim 1, wherein the cavity comprises or consists essentially of bulk metallic glass or bulk metallic glass matrix composite and the cavity is a ring cavity having a spherical or elliptical inner surface.

16. A spectrometer, comprising:
a source of electromagnetic radiation;
a cavity receiving electromagnetic radiation emitted from the source; and
a detector detecting the electromagnetic radiation after multiple passes of the electromagnetic radiation through the cavity;
wherein the cavity comprises a molded surface of a smart phone case or a portable computer case, and
the electromagnetic radiation is reflected from the molded surface to form the multiple passes of the electromagnetic radiation.

17. The spectrometer of claim 16, wherein the smart phone case or the portable computer case consists essentially of molded bulk metallic glass or a composite comprising molded bulk metallic glass.

18. A method of fabricating a smart phone case, comprising:
molding a material into a smart phone case wherein the smart phone case is capable of holding a smart phone and a portable spectrometer, the portable spectrometer including:

a cavity;

a laser for emitting electromagnetic radiation that is directed on the sample in the cavity, wherein the electromagnetic radiation is reflected within the cavity to form multiple passes of the electromagnetic radiation through the sample; and a detector for detecting the electromagnetic radiation after the electromagnetic radiation has made the multiple passes through the sample in the cavity, the detector outputting a signal in response to the detecting and communicating the signal to the smart phone, and the smart phone executing an application that performs a spectral analysis of the signal; and wherein the smart phone case comprises a first opening comprising the cavity, a second opening holding the laser, and a third opening holding the detector.

19. The method of claim 18, wherein the material consists essentially of bulk metallic glass or a composite comprising bulk metallic glass such that the smart phone case consists essentially of the bulk metallic glass or the composite.

20. An apparatus, comprising:
a source of electromagnetic radiation;
a cavity receiving electromagnetic radiation emitted from the source;
a detector detecting the electromagnetic radiation after multiple passes of the electromagnetic radiation through the cavity;
a case for a mobile device, wherein the case holds the source comprising a laser, the cavity, and the detector; and
a wired or wireless connection communicating a signal outputted from the detector in response to the detecting, wherein:
the mobile device, connected to the wired or wireless connection and receiving the signal, executes an application that performs a spectral analysis of the signal, and
the mobile device comprises a tablet, a smart phone, or a laptop.

21. The apparatus of claim 20, wherein the source is a quantum cascade laser and the cavity is a ring cavity.

\* \* \* \* \*